United States Patent
Hickey et al.

(10) Patent No.: US 7,451,761 B2
(45) Date of Patent: Nov. 18, 2008

(54) DRY POWDER INHALERS, RELATED BLISTER PACKAGE INDEXING AND OPENING MECHANISMS, AND ASSOCIATED METHODS OF DISPENSING DRY POWDER SUBSTANCES

(75) Inventors: Anthony James Hickey, Chapel Hill, NC (US); Timothy Crowder, Durham, NC (US); Jeffrey Alan Warden, Raleigh, NC (US); Keith Arthur Johnson, Durham, NC (US); Mark Ennis Ketner, Apex, NC (US); Jay Kinsley Fording, Matthews, NC (US); Michael Duane Garten, Charlotte, NC (US); William Myles Riley, Richmond, VA (US); Sean Derek Anderson, Richmond, VA (US); Bruce Seymour Ferris, Richmond, VA (US); Paul Gilbert Rockwell, Chesterfield, VA (US)

(73) Assignee: Oriel Therapeutics, Inc., Durham, NC (US)

( * ) Notice: Subject to any disclaimer, the term of this patent is extended or adjusted under 35 U.S.C. 154(b) by 825 days.

(21) Appl. No.: 10/970,154

(22) Filed: Oct. 21, 2004

(65) Prior Publication Data
US 2005/0103337 A1     May 19, 2005

Related U.S. Application Data

(60) Provisional application No. 60/514,671, filed on Oct. 27, 2003.

(51) Int. Cl.
*A61M 15/00*     (2006.01)
*A61M 16/00*     (2006.01)
*B05D 7/14*     (2006.01)
*B65D 83/06*     (2006.01)

(52) U.S. Cl. .................... 128/203.21; 128/203.15
(58) Field of Classification Search ............ 128/203.15, 128/203.12, 203.19, 203.21, 200.14, 200.21
See application file for complete search history.

(56) References Cited

U.S. PATENT DOCUMENTS

| | | | |
|---|---|---|---|
| 3,565,070 A | 2/1971 | Hanson et al. | |
| 3,679,010 A | 7/1972 | Bullivant | 177/16 |
| 3,724,720 A | 4/1973 | Bullivant | 222/55 |
| 3,777,874 A | 12/1973 | Birckhead | 406/32 |
| 3,812,854 A | 5/1974 | Michaels et al. | |
| 3,948,264 A | 4/1976 | Wilke et al. | 128/203.15 |
| 3,948,284 A | 4/1976 | Walworth | |
| 3,962,917 A | 6/1976 | Terada | |
| 3,971,377 A | 7/1976 | Damani | |
| 3,989,042 A | 11/1976 | Mitsui et al. | |
| 4,054,784 A | 10/1977 | Ricciardi et al. | 400/240 |
| 4,113,809 A | 9/1978 | Abair et al. | |
| 4,147,166 A | 4/1979 | Hansen | |
| 4,319,155 A | 3/1982 | Nakai et al. | 310/316 |
| 4,381,545 A | 4/1983 | Biddle et al. | 700/240 |
| 4,393,884 A | 7/1983 | Jacobs | |
| 4,446,862 A | 5/1984 | Baum et al. | |
| 4,472,091 A | 9/1984 | Callahan | 406/132 |
| 4,600,855 A | 7/1986 | Strachan | |
| 4,607,254 A | 8/1986 | Carlson | |
| 4,648,393 A | 3/1987 | Landis et al. | |
| 4,778,054 A | 10/1988 | Newell et al. | 206/531 |
| 4,819,629 A | 4/1989 | Jonson | |
| 4,877,989 A | 10/1989 | Drews et al. | |
| 5,063,922 A | 11/1991 | Hakkinen | |
| 5,201,322 A | 4/1993 | Henry et al. | 600/532 |
| 5,349,947 A | 9/1994 | Newhouse et al. | 128/203.21 |
| 5,363,842 A | 11/1994 | Mishelevich et al. | |
| 5,388,572 A | 2/1995 | Mulhauser et al. | 128/203.15 |
| 5,437,271 A | 8/1995 | Hodson et al. | 128/203.15 |
| 5,469,843 A | 11/1995 | Hodson | 128/203.15 |
| 5,482,030 A | 1/1996 | Klein | 128/200.23 |
| 5,482,032 A | 1/1996 | Smith et al. | 128/203.15 |
| 5,497,764 A | 3/1996 | Ritson et al. | 128/200.14 |
| 5,505,196 A | 4/1996 | Herold et al. | 128/203.15 |
| 5,507,277 A | 4/1996 | Rubsamen et al. | 128/200.14 |
| 5,509,404 A | 4/1996 | Lloyd et al. | 128/200.14 |
| 5,520,166 A | 5/1996 | Ritson et al. | 128/200.14 |
| 5,522,378 A | 6/1996 | Ritson et al. | 128/200.14 |
| 5,522,385 A | 6/1996 | Lloyd et al. | 128/203.26 |

| Patent No. | Date | Inventor | Class |
|---|---|---|---|
| 5,533,502 A | 7/1996 | Piper | 128/203.21 |
| 5,542,410 A | 8/1996 | Goodman et al. | 128/200.14 |
| 5,544,646 A | 8/1996 | Lloyd et al. | 128/200.14 |
| 5,558,085 A | 9/1996 | Rubsamen et al. | 128/200.14 |
| 5,577,497 A | 11/1996 | Mecikalski et al. | 128/203.15 |
| 5,583,304 A | 12/1996 | Kalidindi | 73/863.56 |
| 5,608,647 A | 3/1997 | Rubsamen et al. | 364/509 |
| 5,618,177 A | 4/1997 | Abbott | 433/88 |
| 5,619,984 A | 4/1997 | Hodson et al. | 128/203.15 |
| 5,622,162 A | 4/1997 | Johansson et al. | 128/203.12 |
| 5,622,166 A | 4/1997 | Eisele et al. | 128/203.12 |
| 5,642,727 A | 7/1997 | Datta et al. | 128/203.15 |
| 5,655,523 A * | 8/1997 | Hodson et al. | 128/203.15 |
| 5,660,166 A | 8/1997 | Lloyd et al. | 128/200.14 |
| 5,672,581 A | 9/1997 | Rubsamen et al. | 514/3 |
| 5,694,919 A | 12/1997 | Rubsamen et al. | 128/200.14 |
| 5,694,920 A | 12/1997 | Abrams et al. | 128/200.16 |
| 5,699,789 A | 12/1997 | Hendricks | 128/203.15 |
| 5,709,202 A | 1/1998 | Lloyd et al. | 128/200.14 |
| 5,718,222 A | 2/1998 | Lloyd et al. | 128/200.14 |
| 5,724,957 A | 3/1998 | Rubsamen et al. | 128/200.14 |
| 5,724,959 A | 3/1998 | McAughey et al. | 128/203.15 |
| 5,727,546 A | 3/1998 | Clarke et al. | 128/203.15 |
| 5,735,263 A | 4/1998 | Rubsamen et al. | 128/200.14 |
| 5,740,793 A | 4/1998 | Hodson et al. | 128/203.15 |
| 5,743,250 A | 4/1998 | Gonda et al. | 128/200.14 |
| 5,743,252 A | 4/1998 | Rubsamen et al. | 128/200.14 |
| 5,755,218 A | 5/1998 | Johansson et al. | 128/200.14 |
| 5,767,068 A | 6/1998 | VanDevanter et al. | 514/9 |
| 5,770,152 A | 6/1998 | Schuster et al. | 422/73 |
| 5,785,049 A | 7/1998 | Smith et al. | 128/203.15 |
| 5,792,057 A | 8/1998 | Rubsamen et al. | 600/431 |
| 5,813,397 A | 9/1998 | Goodman et al. | 128/200.14 |
| 5,819,726 A | 10/1998 | Rubsamen et al. | 128/200.14 |
| 5,823,178 A | 10/1998 | Lloyd et al. | 128/200.14 |
| 5,823,434 A | 10/1998 | Cooper | 239/102.2 |
| 5,826,570 A | 10/1998 | Goodman et al. | 128/200.14 |
| 5,829,435 A | 11/1998 | Rubsamen et al. | 128/203.21 |
| 5,829,436 A | 11/1998 | Rubsamen et al. | 128/200.14 |
| 5,855,564 A | 1/1999 | Ruskewicz et al. | 604/62 |
| 5,857,456 A | 1/1999 | Sun et al. | 128/203.15 |
| 5,871,010 A | 2/1999 | Datta et al. | 128/203.15 |
| 5,873,358 A | 2/1999 | Gonda et al. | 128/200.14 |
| 5,875,776 A | 3/1999 | Vaghefi | 128/203.15 |
| 5,884,620 A | 3/1999 | Gonda et al. | 128/200.14 |
| 5,888,477 A | 3/1999 | Gonda et al. | 424/45 |
| 5,894,841 A | 4/1999 | Voges | 128/203.12 |
| 5,906,202 A | 5/1999 | Schuster et al. | 128/203.23 |
| 5,906,294 A | 5/1999 | Ikeya et al. | 222/55 |
| D410,541 S | 6/1999 | Moulin | D24/110 |
| 5,910,301 A | 6/1999 | Farr et al. | 424/45 |
| 5,915,378 A | 6/1999 | Lloyd et al. | 128/200.22 |
| 5,921,237 A | 7/1999 | Eisele et al. | 128/203.21 |
| 5,934,272 A | 8/1999 | Lloyd et al. | 128/200.22 |
| 5,938,118 A | 8/1999 | Cooper | 239/102.2 |
| 5,941,240 A | 8/1999 | Gonda et al. | 128/200.14 |
| 5,957,124 A | 9/1999 | Lloyd et al. | 128/200.22 |
| 5,960,609 A | 10/1999 | Abrams et al. | 53/428 |
| 5,960,792 A | 10/1999 | Lloyd et al. | 128/203.22 |
| 5,970,973 A | 10/1999 | Gonda et al. | 128/200.14 |
| 5,971,951 A | 10/1999 | Ruskewicz et al. | 604/62 |
| 5,975,076 A | 11/1999 | Yianneskis et al. | 128/203.15 |
| 5,993,783 A | 11/1999 | Eljamal et al. | 424/46 |
| 6,012,450 A | 1/2000 | Rubsamen | 128/200.14 |
| 6,012,454 A | 1/2000 | Hodson et al. | 128/203.15 |
| 6,014,969 A | 1/2000 | Lloyd et al. | 128/200.14 |
| 6,024,090 A | 2/2000 | Gonda et al. | 128/204.23 |
| 6,026,809 A | 2/2000 | Abrams et al. | 125/203.15 |
| 6,029,663 A | 2/2000 | Eisele et al. | 128/203.21 |
| 6,051,551 A | 4/2000 | Hughes et al. | 514/3 |
| 6,062,214 A | 5/2000 | Howlett | 128/200.23 |
| 6,063,138 A | 5/2000 | Hanna et al. | 23/295 R |
| 6,065,509 A | 5/2000 | Bonney et al. | 141/71 |
| 6,070,575 A | 6/2000 | Gonda et al. | 128/203.12 |
| 6,080,762 A | 6/2000 | Allen et al. | 514/337 |
| 6,085,753 A | 7/2000 | Gonda et al. | 128/898 |
| 6,089,227 A | 7/2000 | Nilsson | 128/203.15 |
| 6,095,134 A | 8/2000 | Sievers et al. | 128/200.14 |
| 6,095,141 A | 8/2000 | Armer et al. | 128/204.26 |
| 6,095,142 A | 8/2000 | Giorgini | 128/205.23 |
| 6,098,615 A | 8/2000 | Lloyd et al. | 128/200.14 |
| 6,098,620 A | 8/2000 | Lloyd et al. | 128/204.23 |
| 6,102,035 A | 8/2000 | Asking et al. | 128/203.15 |
| 6,109,261 A | 8/2000 | Clarke et al. | 128/203.15 |
| 6,116,238 A | 9/2000 | Jackson et al. | 128/203.15 |
| 6,119,953 A | 9/2000 | Gañán-Calvo et al. | 239/8 |
| 6,123,068 A | 9/2000 | Lloyd et al. | 128/200.24 |
| 6,131,567 A | 10/2000 | Gonda et al. | 128/200.14 |
| 6,131,570 A | 10/2000 | Schuster et al. | 128/203.26 |
| 6,142,146 A | 11/2000 | Abrams et al. | 128/203.15 |
| 6,143,277 A | 11/2000 | Ashurst et al. | 424/45 |
| 6,152,130 A | 11/2000 | Abrams et al. | 128/204.21 |
| 6,167,880 B1 | 1/2001 | Gonda et al. | 128/200.14 |
| 6,182,655 B1 | 2/2001 | Keller et al. | 128/203.15 |
| 6,192,876 B1 | 2/2001 | Denyer et al. | 125/205.25 |
| 6,192,882 B1 | 2/2001 | Gonda | 128/203.21 |
| 6,196,218 B1 | 3/2001 | Voges | 128/200.14 |
| 6,208,065 B1 | 3/2001 | Ueyama | 310/328 |
| 6,209,538 B1 | 4/2001 | Casper et al. | 128/203.15 |
| 6,230,706 B1 | 5/2001 | Gonda et al. | 128/203.12 |
| 6,237,590 B1 | 5/2001 | Leedom et al. | 128/203.15 |
| 6,250,298 B1 | 6/2001 | Gonda et al. | 128/200.14 |
| 6,263,872 B1 | 7/2001 | Schuster et al. | 128/203.26 |
| 6,271,206 B1 | 8/2001 | Pillai et al. | 514/44 |
| 6,288,360 B1 | 9/2001 | Beste | 219/121.71 |
| 6,295,986 B1 | 10/2001 | Patel et al. | 128/203.12 |
| 6,296,152 B1 | 10/2001 | Semenenko | 222/199 |
| 6,328,033 B1 | 12/2001 | Avrahami et al. | 128/203.15 |
| 6,335,316 B1 | 1/2002 | Hughes et al. | 514/12 |
| 6,348,209 B2 | 2/2002 | Placke et al. | 624/435 |
| 6,349,719 B2 | 2/2002 | Gonda | 128/200.14 |
| 6,351,984 B1 | 3/2002 | Srinivasan | 73/40.7 |
| 6,351,987 B1 | 3/2002 | Winston et al. | 73/53.01 |
| 6,354,516 B1 | 3/2002 | Patel et al. | 239/331 |
| 6,369,354 B1 | 4/2002 | Beste | 219/121.71 |
| 6,488,181 B1 | 12/2002 | Schuller et al. | 222/161 |
| 6,651,341 B1 | 11/2003 | Myrman et al. | 30/2 |
| 6,805,175 B1 | 10/2004 | Pinkas et al. | 141/130 |
| 6,845,772 B2 | 1/2005 | Braithwaite et al. | 128/203.15 |
| 6,971,383 B2 * | 12/2005 | Hickey et al. | 128/203.15 |
| 7,231,920 B2 * | 6/2007 | Harvey et al. | 128/203.15 |
| 2001/0007853 A1 | 7/2001 | Dimarchi et al. | 514/3 |
| 2001/0053761 A1 | 12/2001 | Dimarchi et al. | 514/3 |
| 2004/0025877 A1 | 2/2004 | Crowder et al. | |
| 2004/0050860 A1 | 3/2004 | Crowder et al. | |
| 2004/0055598 A1 | 3/2004 | Crowder et al. | |
| 2004/0123864 A1 | 7/2004 | Hickey et al. | |
| 2004/0153262 A1 | 8/2004 | Hickey et al. | |
| 2004/0244794 A1 * | 12/2004 | Richards | 128/203.15 |
| 2005/0258182 A1 * | 11/2005 | Anderson | 221/7 |

FOREIGN PATENT DOCUMENTS

| | | |
|---|---|---|
| EP | 0129985 | 1/1985 |
| EP | 1106196 A | 6/2001 |
| EP | 1166812 A | 1/2002 |
| EP | 1172122 A1 | 1/2002 |
| EP | 1021335 | 6/2003 |
| JP | 58-067330 | 4/1983 |
| WO | WO 99/19215 | 4/1999 |
| WO | WO99/65551 | 12/1999 |
| WO | WO 01/68169 A | 9/2001 |
| WO | WO 01/68169 A1 | 9/2001 |
| WO | WO 2004/002827 | 1/2004 |
| WO | PCT/US2004/035424 | 10/2004 |
| WO | PCT/US2004/035433 | 10/2004 |

| WO | WO 2005002654 A2 | 1/2005 |
| WO | WO 2005002654 A3 | 1/2005 |

OTHER PUBLICATIONS

U.S. Appl. No. 11/052,627, Warden.
Brown et al., *Piezo-Electronic Inhaler*, Drug Delivery Technology, vol. 4, No. 8, pp. 90-93, (Oct. 2004).
Crowder et al., *2001: an Odyssey in Inhaler Formulation and Design*, Pharmaceutical Technology, pp. 99-113 (Jul. 2001).
Hickey et al., *A new millennium for inhaler technology*. 21 Pharm. Tech., n. 6, pp. 116-125 (1997).
Peart et al., *New Developments in Dry Powder Inhaler Technology*, American Pharmaceutical Review, vol. 4, n.3, pp. 37-45 (2001).
Prime et al., *Review of Dry Powder Inhalers*, 26 Adv. Drug Delivery Rev., pp. 51-58 (1997).
Wolff et al., *Generation of Aerosolized Drugs*, J. Aerosol. Med. pp. 89-106 (1994).
http://advair.ibreathe.com/consumer/2_2_2_taking_advair_animation.htm, Advair Diskus 100/50, 3 sheets (1997).
http://aventis.co.uk/main/0,1003,EN-GB-29939-48165—,FF.html, Aventis Pharma UK, Dry Powder Inhaler (DPI) Delivery Platforms, 1 sheet, 2005.

\* cited by examiner

*Primary Examiner*—Justine R Yu
*Assistant Examiner*—Kristen C Matter
(74) *Attorney, Agent, or Firm*—Myers, Bigel, Sibley & Sajovec, P.A.

(57) ABSTRACT

Dry powder inhalers with a multi-dose dry powder package for dispensing pharmaceutical grade formulations of inhalable dry powder, include: (a) a blister package comprising a plurality of spaced apart sealed blisters thereon, each blister having a projecting ceiling and a floor defining a blister channel therebetween, the blister channel comprising a dry powder therein; (b) a movable blade cartridge holding a blade at a forward portion thereof; and (c) an extendable mouthpiece attached to the movable blade cartridge. In operation, a user pulls the mouthpiece outward and then pushes the mouthpiece inward to cause the blister package to advance to position a blister in a selected dispensing position in the inhaler and to cause the blade cartridge to move the blade across a blister ceiling held in the dispensing position in the inhaler to thereby open the blister held in the dispensing position.

52 Claims, 26 Drawing Sheets

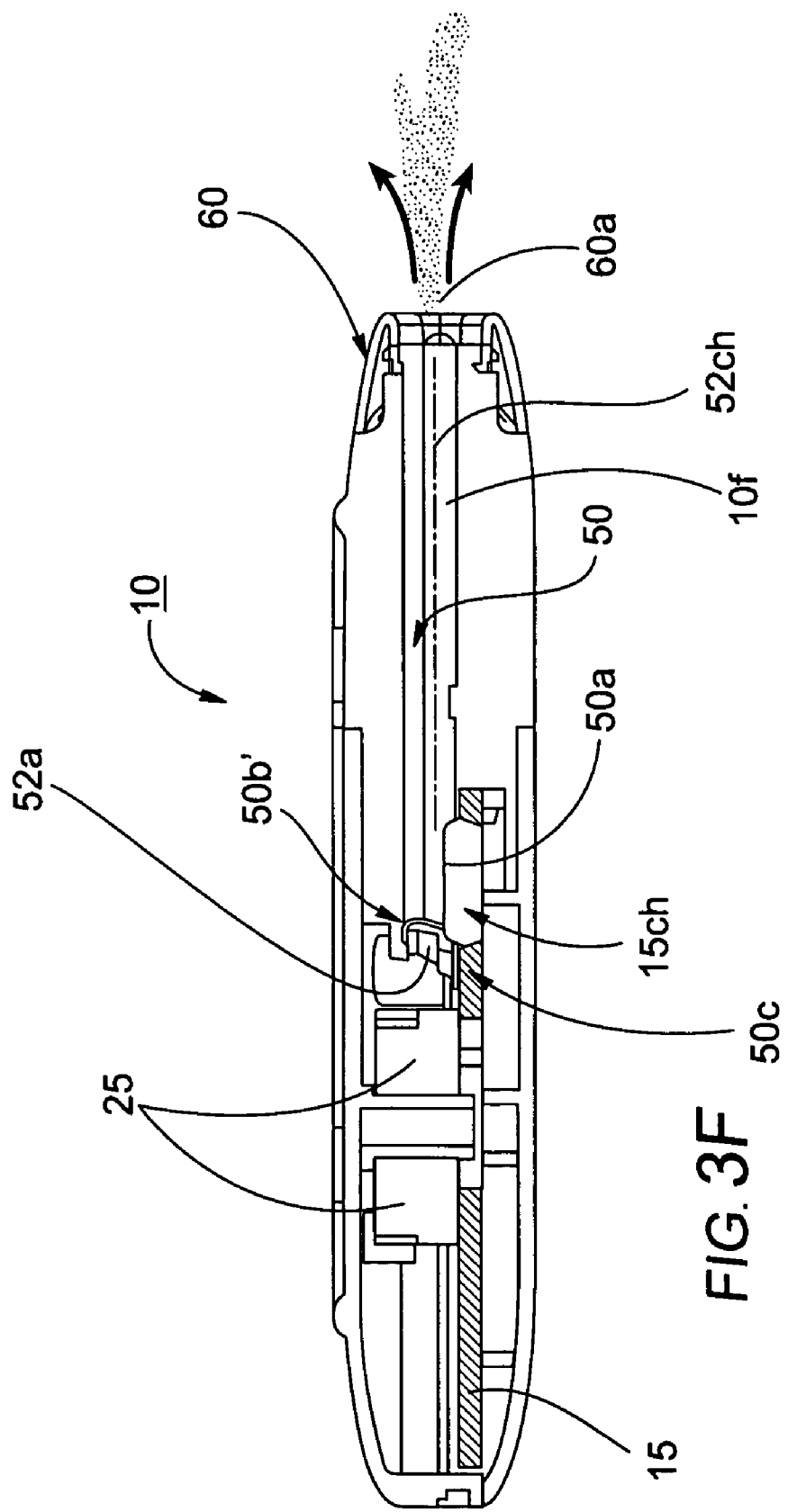

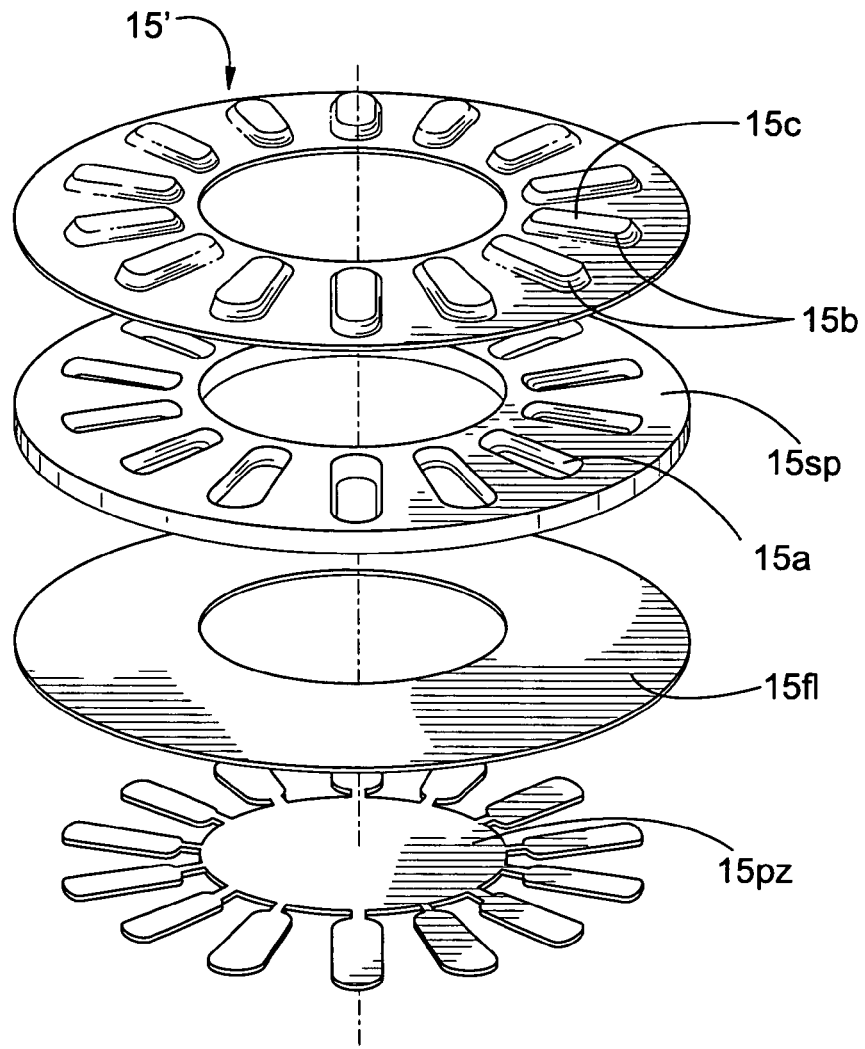
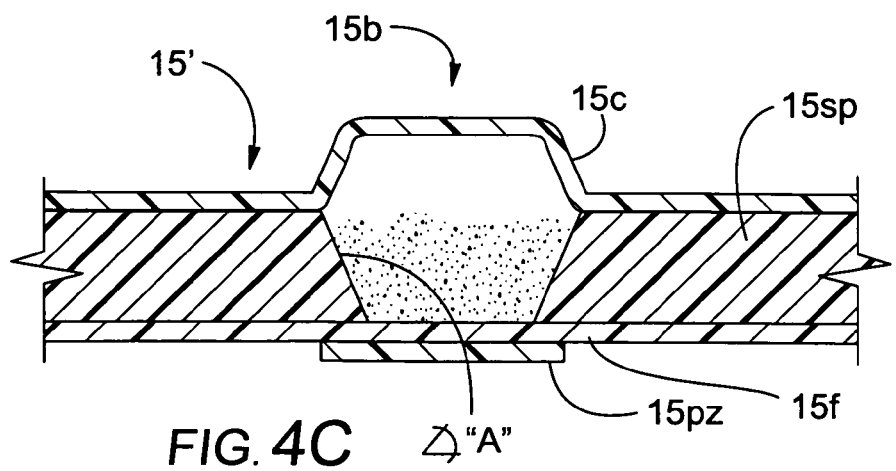
FIG. 4B
FIG. 4C

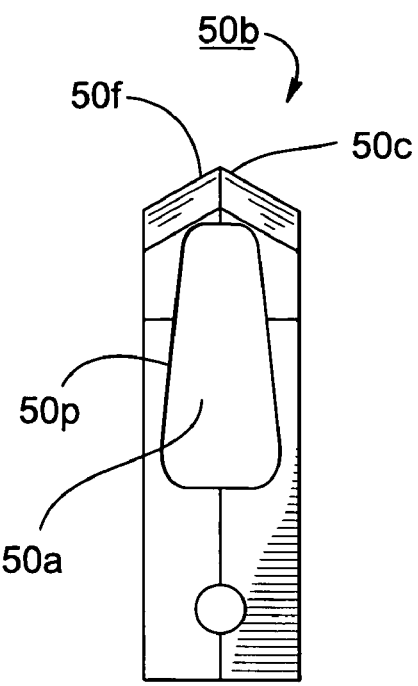
FIG. 6B
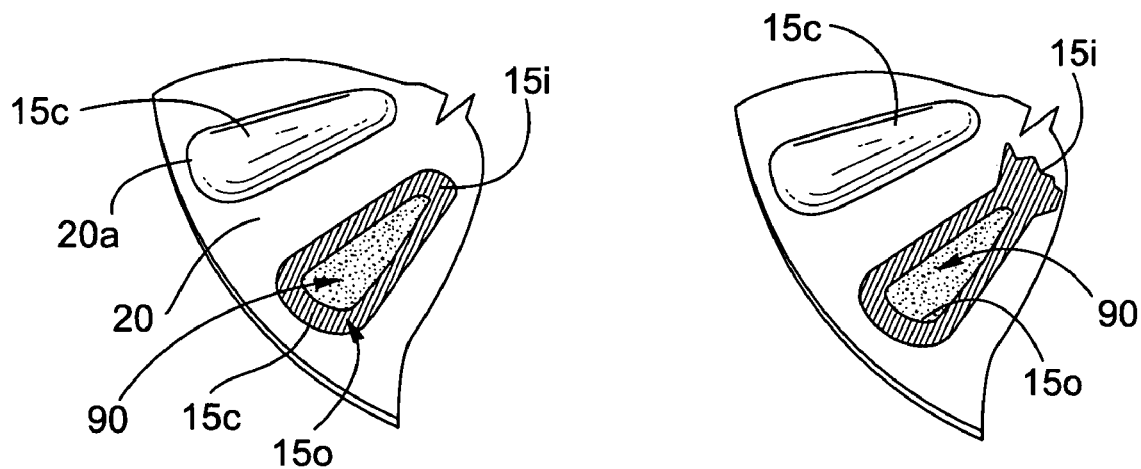
FIG. 6C
FIG. 6D

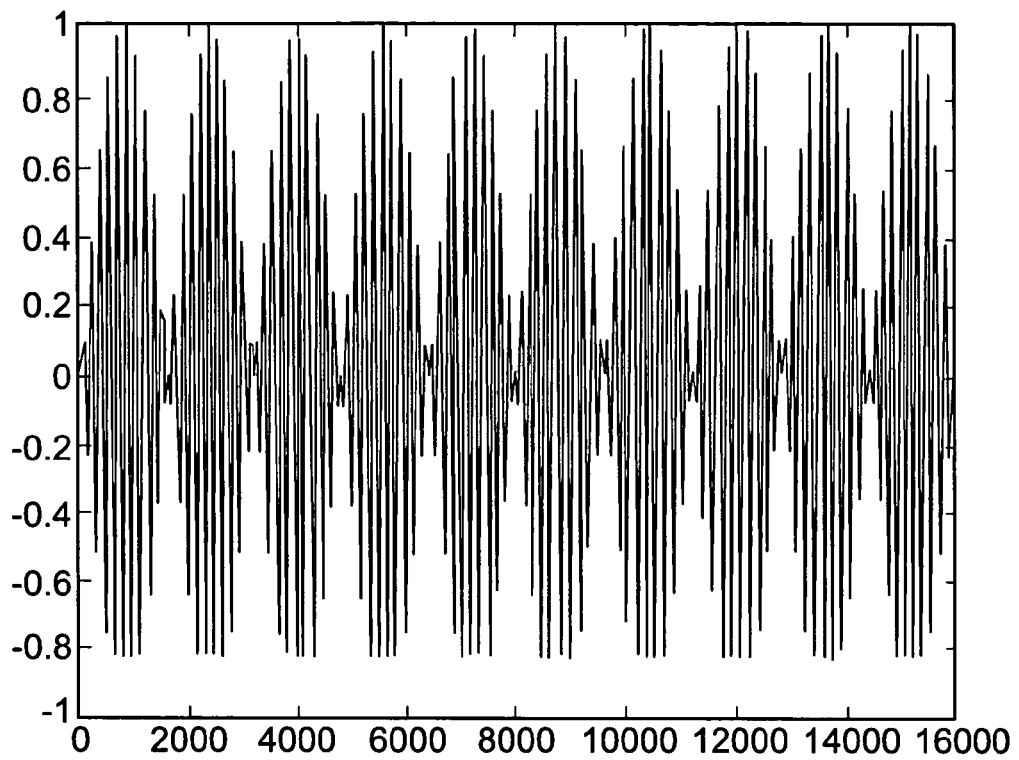
FIG. 11A
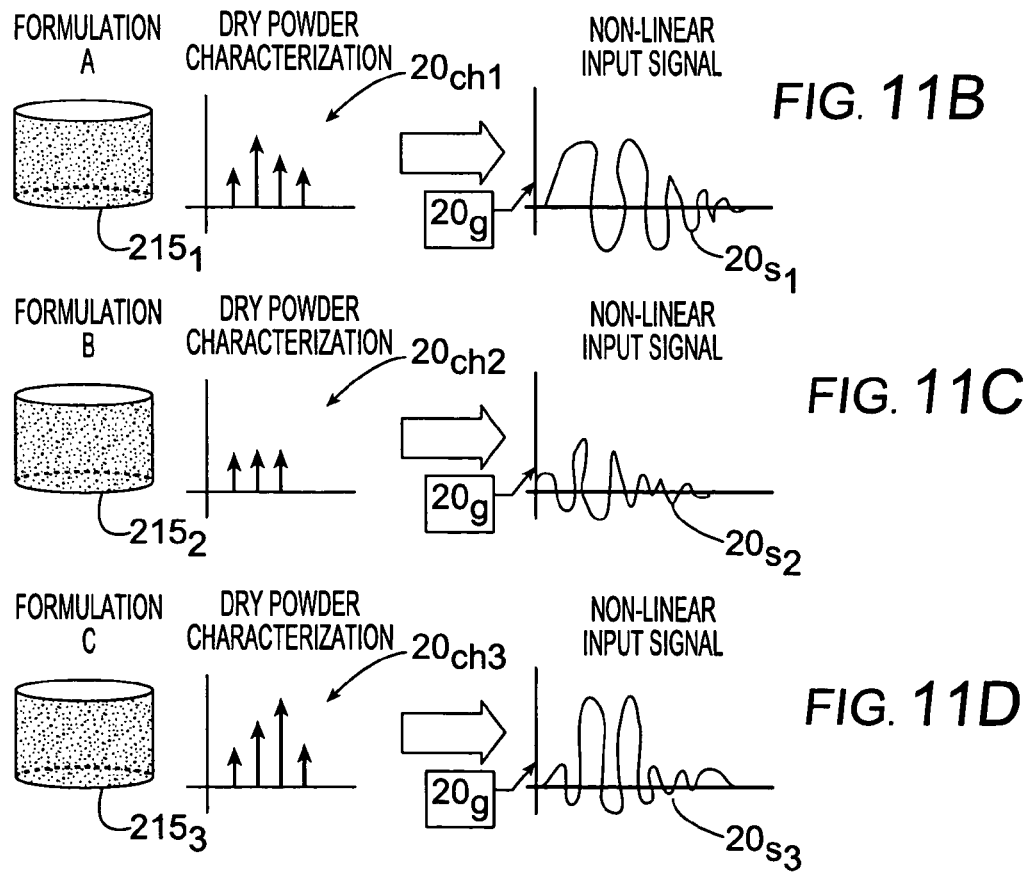
FIG. 11B
FIG. 11C
FIG. 11D

DRY POWDER INHALERS, RELATED BLISTER PACKAGE INDEXING AND OPENING MECHANISMS, AND ASSOCIATED METHODS OF DISPENSING DRY POWDER SUBSTANCES

RELATED APPLICATION

This application claims priority to U.S. Provisional Application Ser. No. 60/514,671, filed Oct. 27, 2003, the contents of which are hereby incorporated by reference as if recited in full herein.

FIELD OF THE INVENTION

The present invention relates to the delivery of dry powder substances, such as dose-regulated pharmaceutical products, as inhalant aerosols.

BACKGROUND OF THE INVENTION

Dry powder inhalers (DPI's) represent a promising alternative to pressurized pMDI (pressurized meted dose inhaler) devices for delivering drug aerosols without using CFC propellants. See generally, Crowder et al., 2001: *an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n.3, pp. 37-45 (2001). Typically, the DPIs are configured to deliver a powdered drug or drug mixture that includes an excipient and/or other ingredients. Conventionally, many DPIs have operated passively, relying on the inspiratory effort of the patient to dispense the drug provided by the powder. Unfortunately, this passive operation can lead to poor dosing uniformity because inspiratory capabilities can vary from patient to patient (and sometimes even use-to-use by the same patient, particularly if the patient is undergoing an asthmatic attack or respiratory-type ailment which tends to close the airway).

Generally described, known single and multiple dose dry powder DPI devices use: (a) individual pre-measured doses, such as capsules containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form (such as a particulate size) of the dry powder into a patient's airway and direct it to a desired deposit site(s). If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, many dry powder inhalers can retain a significant amount of the drug within the device, which can be especially problematic over time. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of these patents are hereby incorporated by reference as if stated in full herein.

More recently, Hickey et al., in U.S. patent application Ser. No. 10/434,009 and PCT Patent Publication No. WO 01/68169A1 and related U.S. National Stage patent application Ser. No. 10/204,609, have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems. The contents of these documents are hereby incorporated by reference as if recited in full herein.

Notwithstanding the above, there remains a need for easily used, cost effective, and/or reliable dry powder inhalers.

SUMMARY

Embodiments of the present invention provide dry powder inhaler configurations and related operational devices. The dry powder inhalers may be particularly suitable for use with active piezoelectric polymer-driven dispersion or delivery means. Particular embodiments of the present invention are directed to dry powder inhaler indexing systems and drug release mechanisms for blister packages, as well as methods for dispensing dry powder substances.

Some embodiments of the present invention are directed to dry powder inhalers with a multi-dose dry powder package for dispensing pharmaceutical grade formulations of inhalable dry powder. The inhalers include: (a) an inhaler housing; (b) a blister package held in the housing, the blister package comprising a plurality of spaced apart sealed blisters thereon, each blister having a projecting ceiling and a floor defining a blister channel therebetween, the blister channel comprising a dry powder therein; (c) a movable blade cartridge mounted in the housing configured to hold a blade at a forward portion thereof; and (d) an extendable mouthpiece attached to the movable blade cartridge. In operation, a user extends the mouthpiece outward and then retracts the mouthpiece inward to cause the blister package to advance thereby positioning a blister in a selected dispensing position in the inhaler, the retraction causing the blade cartridge to move the blade lengthwise across a blister ceiling held in the dispensing position in the inhaler to open the blister held in the dispensing position.

Other embodiments are directed to methods of dispensing dry powder from an inhaler. The methods include: (a) extending a mouthpiece of an inhaler outward to automatically index a blister on a blister package into a dispensing position; (b) vibrating the indexed blister; and (c) retracting the mouthpiece inward to open the indexed blister.

In some embodiments, the extending step can be carried out by manually pulling a mouthpiece of an inhaler outward and the retracting step can be carried out by manually pushing the mouthpiece inward. The vibrating step may be carried out before, after and/or during the retracting step.

In particular embodiments, the opening step comprises automatically advancing a cutting blade across a portion of a projecting ceiling of a blister in the inhaler responsive to the pushing step. The method may also include automatically indexing a blister on a blister package to a dispensing position responsive to the pulling step.

Other embodiments are directed toward blister packaging opening mechanisms adapted for use in an inhaler. The mechanisms include a translatable cutting cartridge having a cutting blade with an aperture formed in the cartridge and/or blade. In operation, the aperture defines a portion of an inspiratory exit flow path. The cutting cartridge is configured to mount to an inhaler and move forward in the inhaler to cause the cutting blade to slice across a projecting ceiling portion of an aligned blister that is sealing a blister channel, traveling generally lengthwise over the blister (typically, generally parallel to the primary surface of the frame member and the underlying blister channel), to open the blister for dispensing a dry powder medicament held therein.

Still other embodiments are directed toward blister packaging opening mechanisms for use in an inhaler that include a translatable cutting cartridge having a plow cutting cartridge. The cutting cartridge is configured to mount to an inhaler and move in the inhaler across a blister (in a substantially lengthwise direction) to cause the cutting blade to substantially concurrently open and fold portions of a projecting ceiling of an aligned blister to open the blister for dispensing a dry powder medicament held therein.

In particular embodiments, the cutting cartridge has a body with a chamber positioned rearward of the cutting blade that, in operation, defines a portion of an inspiratory exit flow path.

Other embodiments are directed to methods for opening a sealed blister on a blister package. The methods include advancing a plow mechanism across a sealed blister to open a projecting ceiling layer thereof to automatically lift and fold a loose edge portion of the opened ceiling layer.

In particular embodiments, the methods can also include slicing the sealed blister open and then using the plow mechanism to lift and fold the loose edge portion. In some embodiments, the plow mechanism comprises a slicing blade positioned at a bottom forwardmost portion thereof, and the slicing step is carried out automatically in response to the advancing step.

Yet other embodiments are directed toward blister package indexing mechanisms adapted for use in an inhaler. The mechanisms include: (a) a blister package having a plurality of spaced apart sealed blisters thereon; (b) a rotating gear having circumferentially spaced apart gear teeth, the gear mounted to the blister package so that the blister package rotates with the gear; and (c) a pawl configured, in operation, to controllably engage at least one gear tooth to urge the gear to rotate in a desired direction to serially index a respective blister on the package to a dispensing position in an inhaler.

It is noted that aspects of the invention may be embodied as hardware, software or combinations of same, i.e., devices and/or computer program products. These and other objects and/or aspects of the present invention are explained in detail in the specification set forth below.

BRIEF DESCRIPTION OF THE DRAWINGS

FIG. 3F is a side sectional view of the inhaler shown in FIG. 3C.

FIG. 4B is an exploded view of an alternate blister package according to embodiments of the present invention.

FIG. 4C is a partial side sectional view of a blister in the blister package shown in FIG. 4B according to embodiments of the present invention.

FIG. 6B is a top view of the cutting member shown in FIG. 6A.

FIG. 6C is a partial top view of a blister package and frame with an exemplary opened blister ceiling configuration according to embodiments of the present invention.

FIG. 6D is a partial top partial view of a blister package and frame with a different opened blister ceiling configuration according to other embodiments of the present invention.

FIG. 11A is a graph of an exemplary vibratory input powder excitation signal according to embodiments of the present invention.

FIGS. 11B-11D are schematic illustrations of dry powder specific non-linear input signals according to embodiments of the present invention.

DESCRIPTION OF EMBODIMENTS OF THE INVENTION

Figure 1:
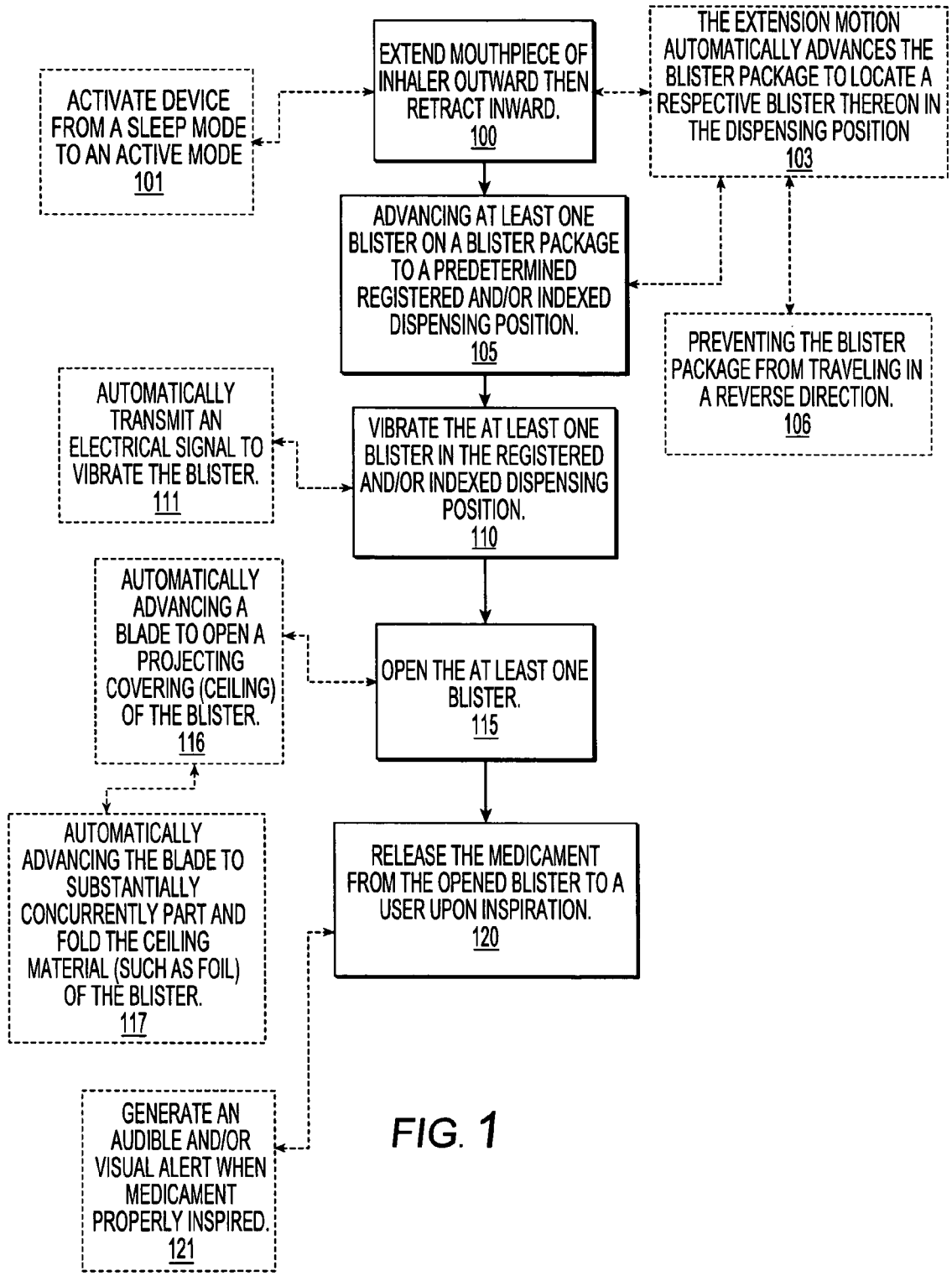
FIG. 1 is a flow chart of operations that can be used to carry out embodiments of the present invention.
Figure 2:
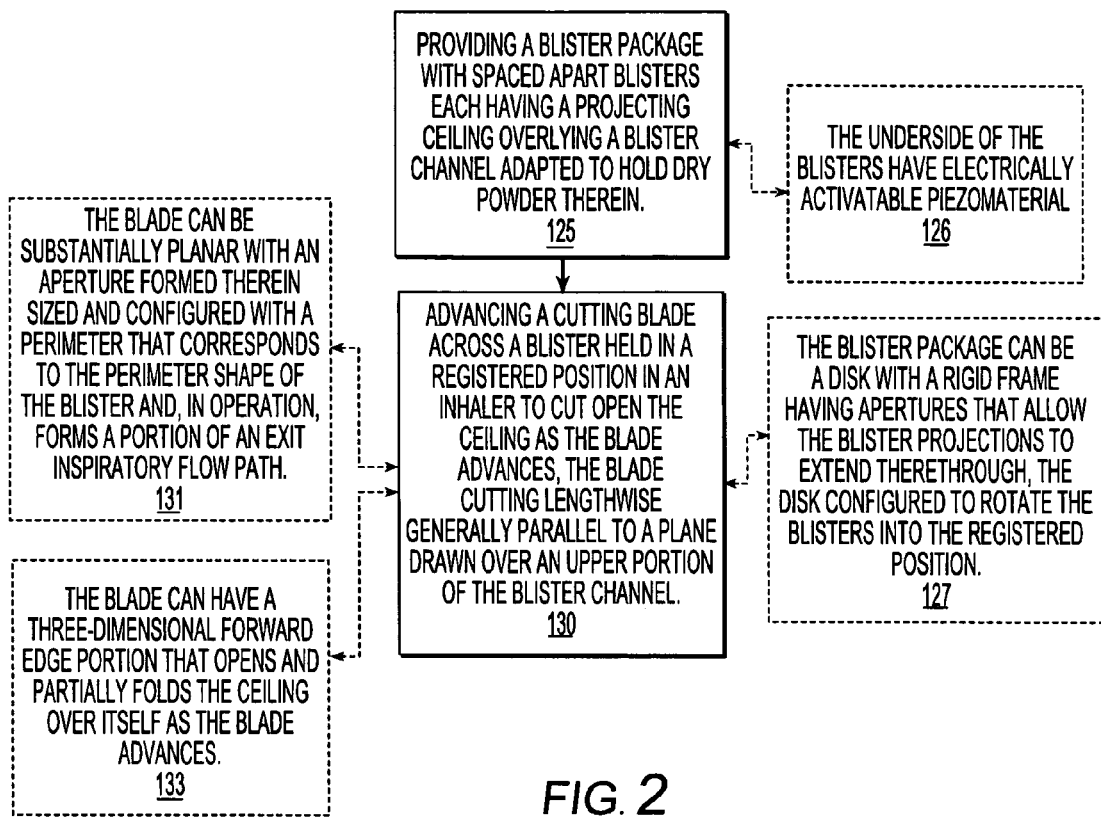
FIG. 2 is a flow chart of operations that can be used to carry out additional embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise. Where used, the terms "attached", "connected", "contacting", and the like, can mean either directly or indirectly, unless stated otherwise.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions.

It will be understood that the spatially relative terms are intended to encompass different orientations of the device in use or operation in addition to the orientation depicted in the figures. For example, if the inhaler in the figures is inverted (turned over), elements described as "below" or "beneath" other elements or features would then be oriented "above" the other elements or features. Thus, the exemplary term "below" can encompass both an orientation of above and below. The device may be otherwise oriented (rotated 90 degrees, 180 degrees, or at other orientations) and the spatially relative descriptors (such as, but not limited to, vertical, horizontal, above, upper, lower, below and the like) used herein interpreted accordingly.

The term "blister" means a sealable dry powder receptacle that can hold a (typically meted) quantity of a dry powder product. The term "blister package" describes a device that holds a plurality of sealed blisters and may be also known as a drug containment system ("DCS"). The blisters may be configured with an elongated channel or cavity with a projecting ceiling as will be described further below, or configured in other suitable geometries. The term "blade" refers to an instrument (typically comprising a sharp knife or razor-like edge) that can slice, puncture, tear or otherwise open, cut, or part a target portion of a sealed blister (typically the ceiling). The terms "plow" and "plow-like" describe a three-dimensional member such as a blade and/or cartridge that, in operation (similar to a snow plow or "cow catcher"), advances across a target portion of an aligned blister and separates (i.e., pushes) target blister material apart while substantially concurrently advancing so that at least one loose end portion of the separated blister material, folds over underlying blister (typically ceiling) material to thereby clear the ceiling material and provide a sufficiently wide open space over the blister that is free of covering material. The term "pawl" refers to a component (such as an arm member) that is configured to engage a gear, ratchet or other mechanism, in at least one predetermined direction, to cause the gear, ratchet or other mechanism to rotate or travel in the desired direction.

The devices and methods of the present invention may be particularly suitable to dispense dry powder substances to in vivo subjects, including animal and, typically, human subjects. The dry powder substance may include one or more active pharmaceutical constituents as well as biocompatible additives that form the desired formulation or blend. As used herein, the term "dry powder" is used interchangeably with "dry powder formulation" and means the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aerorolization delivery to the desired systemic target. The dry powder drug formulations can include active particulate sizes that vary. The device may be particularly suitable for dry powder formulations having particulates which are in the range of between about 0.5-50 μm, typically in the range of between about 0.5 μm -20.0 μm, and more typically in the range of between about 0.5 μm -8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated with embodiments of the invention include, but are not limited to, asthma, COPD (chronic obstructive pulmonary disease), viral or bacterial infections, influenza, allergies, and other respiratory ailments as well as diabetes and other related insulin resistance disorders. The dry powder inhalant administration may be used to deliver locally acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled *Method for Administering ASPB*28-*Human Insulin* and U.S. Patent Application Publication No. 20010007853, entitled *Method for Administering Monomeric Insulin Analogs*, the contents of which are hereby incorporated by reference as if recited in full herein.

Typical dose amounts of the unitized dry powder mixture dispersed in the inhaler will vary depending on the patient size, the systemic target, and the particular drug. Conventional exemplary dry powder dose amount for an average adult is about 10-30 mg and for an average adolescent pediatric subject is from about 5-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular dose receptacle may be formulated as an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In certain embodiments, the active elements are integral to/included as part of the disposable drug package, unlike many conventional active dispersion systems, so cleansing of the active mechanism portion of the inhaler may not be required.

Referring to FIG. 1, in operation, an inhaler mouthpiece can be extended and retracted (i.e., pulled out and pushed in) (block 100). The extension (pulling action) can activate the device from a sleep or off mode to an active mode (block 101). In operation, at least one blister on a blister package can be advanced to a predetermined (i.e., registered) dispensing position (block 105). The extension (pulling motion) can be automatically carried out and/or cause the blister to automatically advance to the dispensing position (block 103). The inhaler can be configured to prevent the blister package from traveling in a reverse direction (block 106). The at least one blister in the dispensing position can be vibrated (block 110).

A selected electrical signal can be automatically transmitted to the blister to cause the vibration (block 111). The at least one blister positioned at the dispensing location can be opened (block 115). The vibration can be carried out after the blister is opened to facilitate or carry out the dispersion and before (such as to position or prime the powder in the blister) and/or during the opening of the blister.

The dry powder (typically a medicament) can be released from the opened blister to a user upon inspiration (block 120). The blister can be opened by automatically advancing a blade to open a projecting ceiling or covering on the blister in response to the retraction (pushing motion) (block 116). The retraction can be automatically or manually carried out. The blade can be configured to automatically advance toward an aligned blister to part and fold the covering (which can contain foil) forming the ceiling of the at least one blister (block 117). An alert can be generated (audible and/or visual) when the medicament is properly inspired or released from the blister to the user (block 121).

FIG. 2 illustrates exemplary opening operations for a blister package. As shown, a blister package with spaced apart sealed blisters is provided, each blister having a projecting ceiling overlying a blister channel adapted to hold dry powder therein (block 125). In certain embodiments, the underside of the blisters can include selective electrically activatable piezomaterial (block 126). A cutting blade can advance across a blister held in a registered position in an inhaler to cut open the ceiling as the blade advances, traveling and slicing and/or cutting generally parallel to an upper primary surface of the frame (typically substantially lengthwise) above the blister channel (block 130).

In certain embodiments, the blister package can be a disk having a substantially rigid frame with apertures that allow the blister projections to extend therethrough. The disk can be attached to the blister package so that as the frame rotates, the blister package rotates to advance a respective blister into the registered position (block 127). In other embodiments, the disk can include a spacer layer that defines at least a portion of a sidewall(s) of the blister channel that rotates to advance the blister (see, e.g., FIG. 4B).

In certain embodiments, the blade can be substantially planar with an aperture formed therein. The aperture can be sized and configured to correspond to the perimeter shape of the blisters. In operation, the aperture can form a portion of an exit inspiratory flow path through which the dry powder of the blister flows to the user (block 131). In some embodiments, the opening member (i.e., blade cartridge) can have a three-dimensional forward edge portion that opens and at least partially folds the ceiling over on itself as the blade advances (block 133).

FIGS. 3A-3F illustrate one embodiment of a dry powder inhaler 10. The top portion of the inhaler is not illustrated so that certain internal components can be more clearly illustrated. FIGS. 3A through 3F illustrate an example of a thin profile inhaler 10 with an extendable mouthpiece 60 according to some embodiments of the present invention. It is noted that FIGS. 3G, 3H and 10A, 10B illustrate a bench prototype model of an inhaler 10 with a retractable/extendable cutting cartridge 50 and other mechanisms and features that can be incorporated into a dry powder inhaler.

Figure 3A:
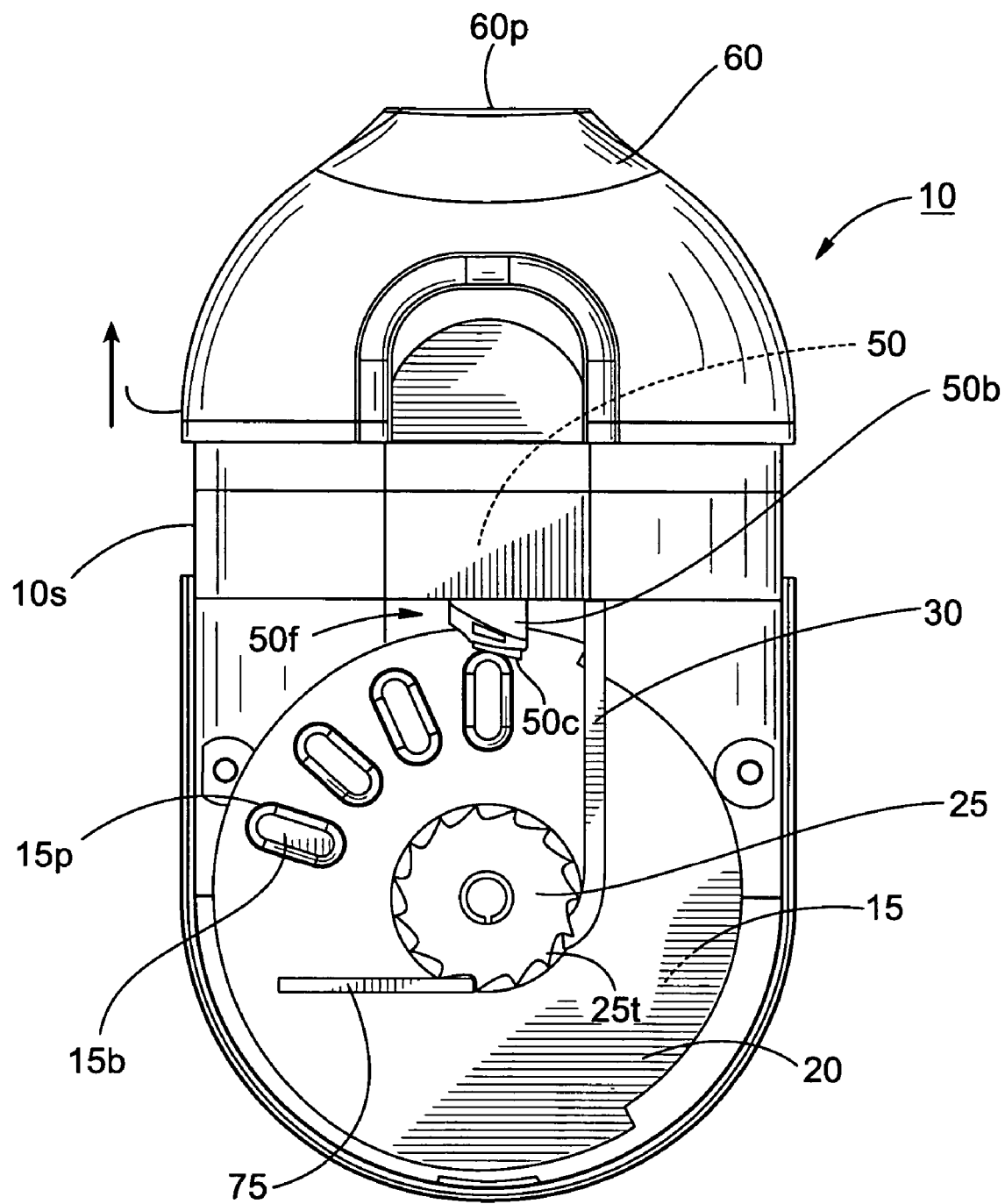
FIG. 3A is an enlarged partial cutaway top view of an exemplary inhaler with the mouthpiece in an extended configuration according to embodiments of the present invention.

As shown in FIG. 3A, the inhaler 10 includes a blister package 15 (see also FIG. 5B) with a plurality of spaced apart blisters 15b (where the number of blisters can be represented as 15b<sub>i</sub>, where i=1 to n). A blister frame 20 may overlay the blister package 15b. As shown, the inhaler 10 also includes a rotably mounted gear 25 with gear teeth 25t, a pawl 30, a translatable cutting cartridge 50 with forward cutting blade 50b and locking arm 75. In some embodiments, and as shown in FIGS. 3A and 3C, the cutting cartridge 50 can be held in the inhaler 10 upstream of the mouthpiece 60 and the mouthpiece 60 can be retractably configured so as to be extended and retracted with the cutting cartridge 50 so as to move substantially in concert with the mouthpiece 60 to automatically carry out the indexing and blister opening operations.

The gear and blister package 15b and/or frame 20 can be configured to rotate in concert (movement of the gear causes movement of the blister package 15 to controllably rotate a blister 15b into a dispensing position. The inhaler 10 also includes a mouthpiece 60 which may be configured to retract and extend in concert with the cutting cartridge 50 as indicated in FIGS. 3A and 3C. The inhaler 10 can also include a locking arm 75 that, in operation, can contact a gear tooth 25t to brace and inhibit the gear 25 (and/or the blister package 15b) from counter rotating away from the dispensing position 10d.

In other embodiments, the mouthpiece 60 may be statically mounted to the inhaler body 10h and/or so that the cutting cartridge 50 moved independently thereof (not shown).

FIG. 3A illustrates a cutting or blade cartridge 50 positioned at an outward (extended) position. Typically, the cutting cartridge 50 is extended outward toward a user (and away from the inside of the inhaler body) to initiate an inhalation use of the device 10. FIG. 3C illustrates the cutting cartridge 50 retracted (translated inward) and positioned over an aligned blister 15b. Thus, a user can, according to some embodiments, extend then retract (pull, then push) the cutting cartridge 50 to automatically open the aligned blister 15b and carry out the dispensing operations. As noted above, the extension and/or retraction can be manually performed by the user and/or automatically performed by a powered inhaler translation or drive mechanism (not shown).

Figure 3B:
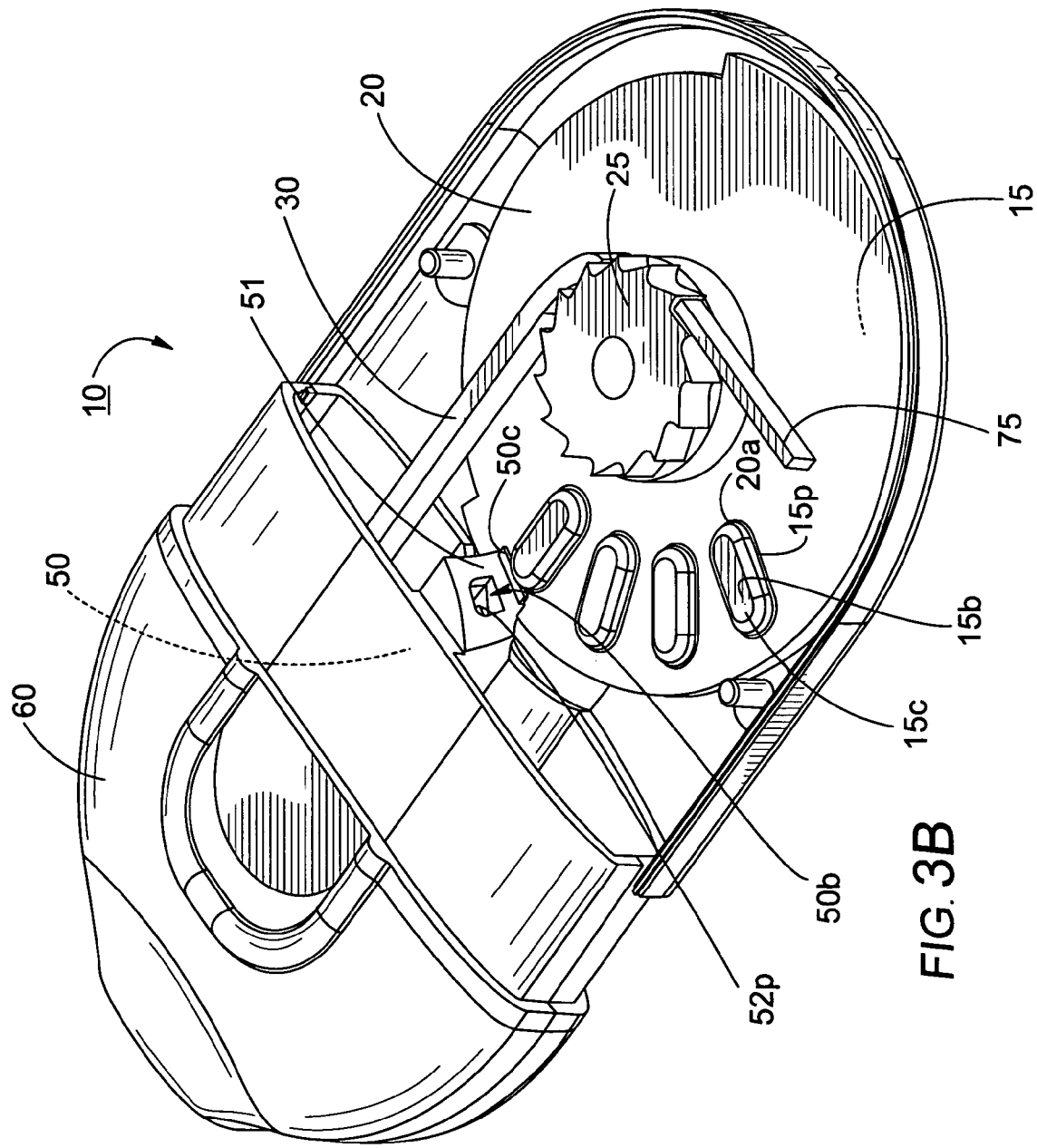
FIG. 3B is an enlarged partial cutaway perspective view of the inhaler shown in FIG. 3A.
Figure 3C:
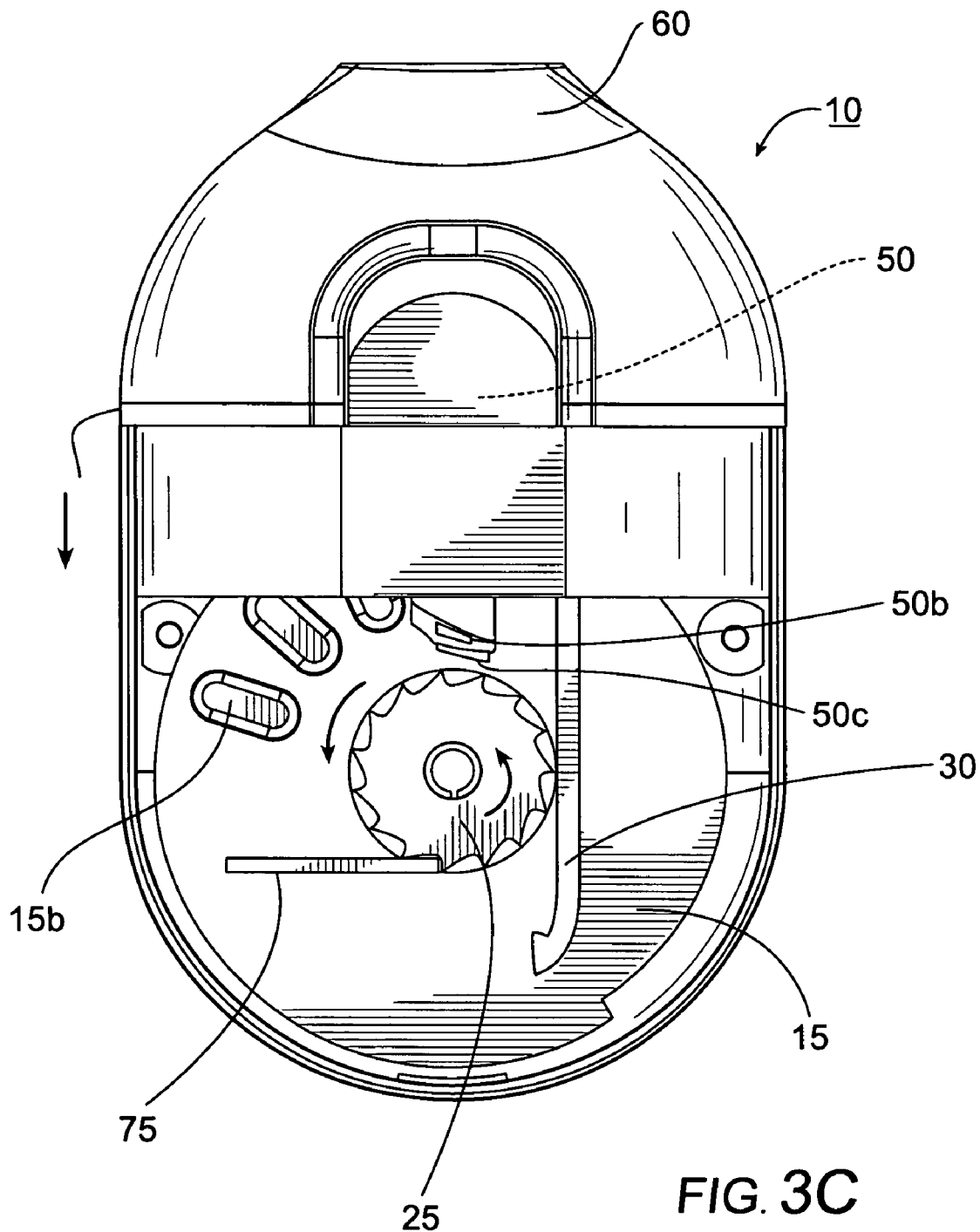
FIG. 3C is an enlarged partial cutaway top view of the inhaler shown in FIG. 3A illustrating the mouthpiece in a retracted configuration according to embodiments of the present invention.
Figure 3D:
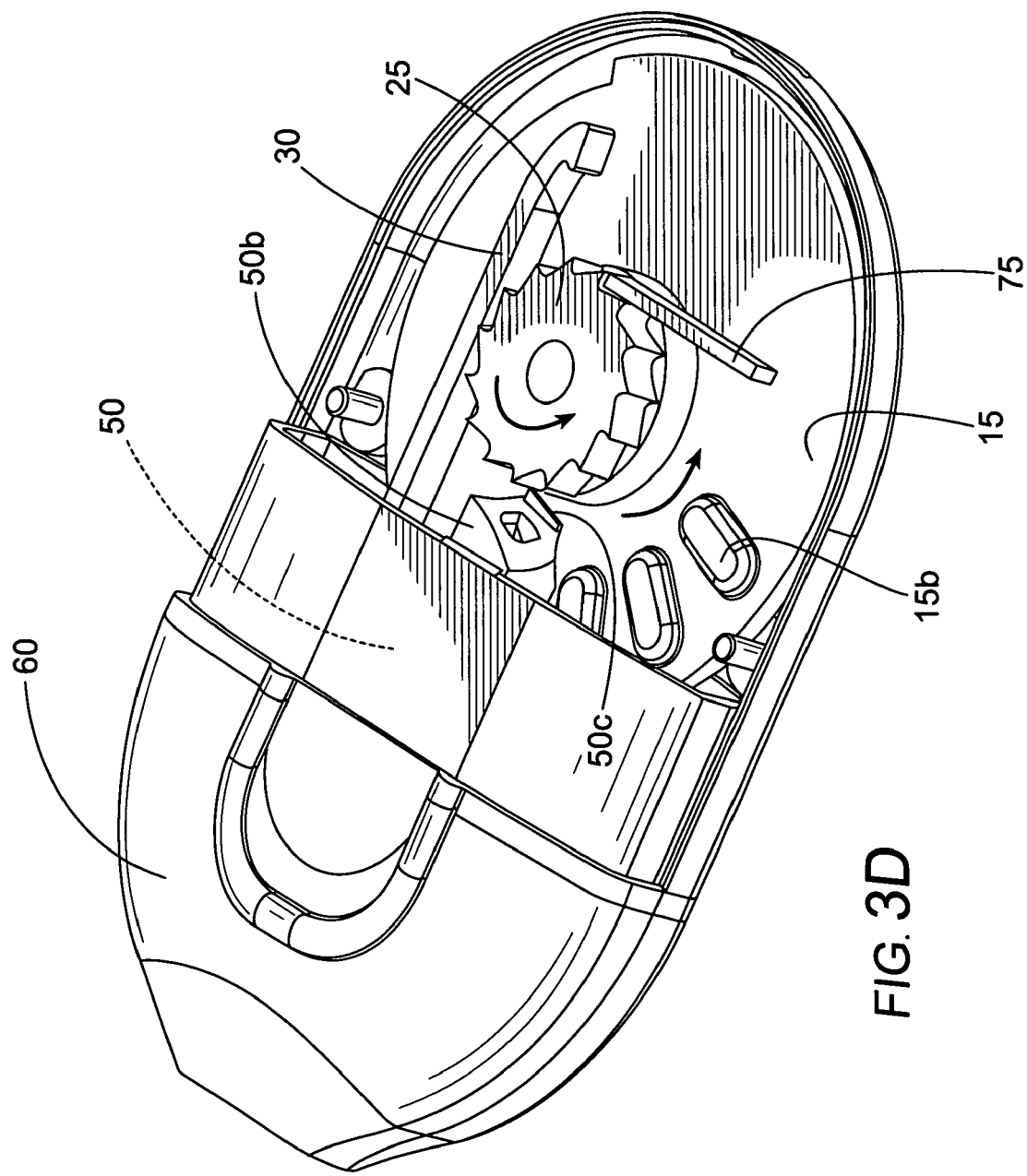
FIG. 3D is an enlarged partial cutaway side perspective view of the inhaler in the retracted configuration shown in FIG. 3C.
Figure 3E:
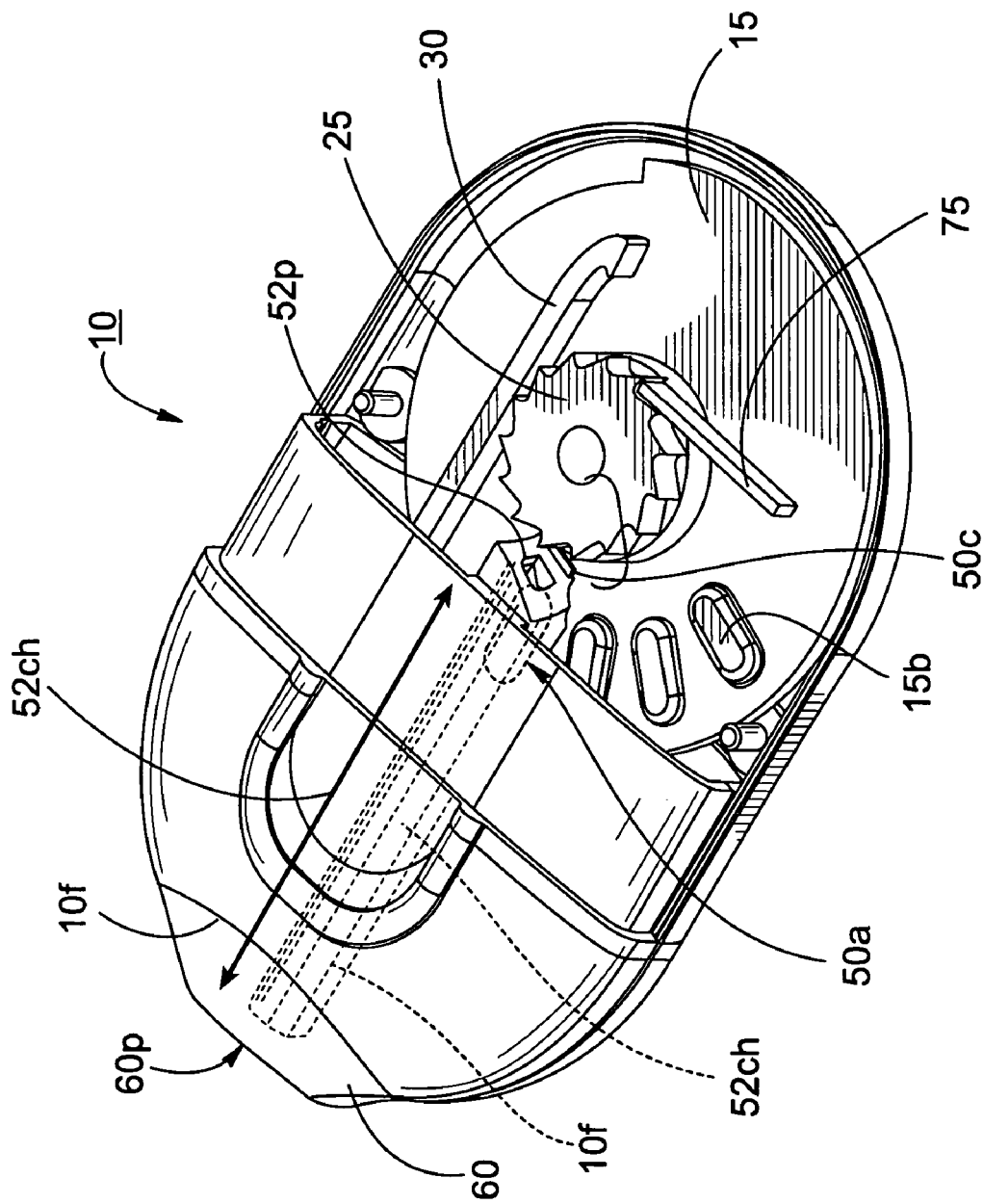
FIG. 3E is an enlarged partial cutaway view of the inhaler shown in FIG. 3C with the mouthpiece in a retracted configuration ready for inpiratory use according to embodiments of the present invention.

Still referring to FIGS. 3A-3F, the blade 50b and/or cutting cartridge 50 can have a lower body with an aperture 50a that is sized and configured similar to the perimeter 15p of a portion of the projecting ceiling 15c of the blister and/or frame aperture 20a. In operation, at its inward operative position, the blade 50b is positioned over the blister channel 15ch with the blade aperture 50a aligned over the frame aperture 20a (where used) and/or aligned blister 15b so that the blade aperture 50a snugly surrounds a target perimeter 15p of the blister channel 15ch to substantially seal the surrounded blister 15b. The blade 50b can remain in this position while the dry powder 90 (FIG. 6D) is dispensed from the blister 15b, responsive to inhalation (inspiration) by a user. Thus, the blade aperture 50a can define a portion of the exit inhalation flow path 10f (FIG. 3E). The cutting cartridge 50 can include a body 52 that defines an elongate channel 52ch that is in fluid communication with (and/or defines) the blade aperture 50a.

Figure 10A:
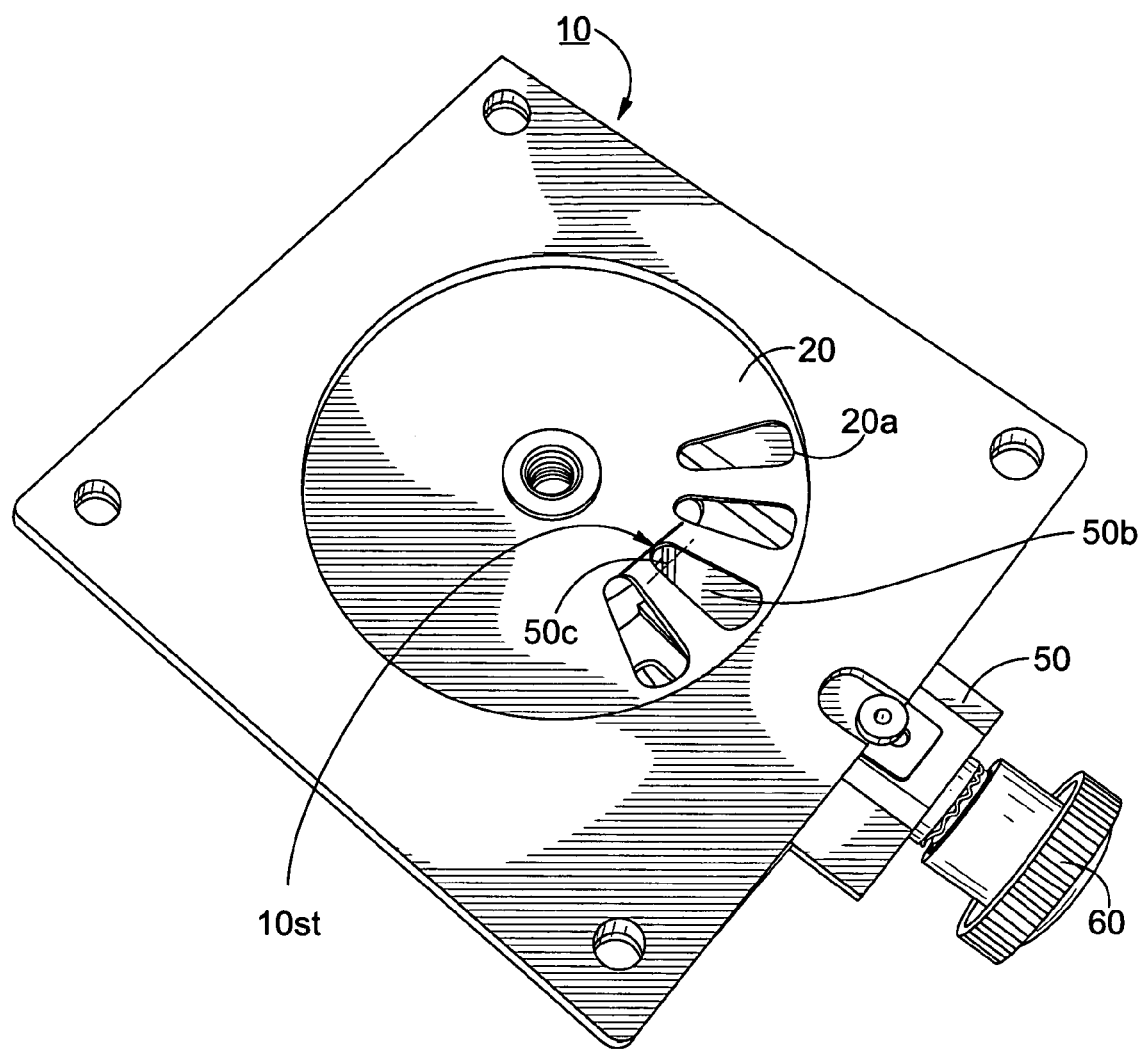
FIG. 10A is a top perspective view of a device similar to that shown in FIG. 3B according to embodiments of the present invention.
Figure 10B:
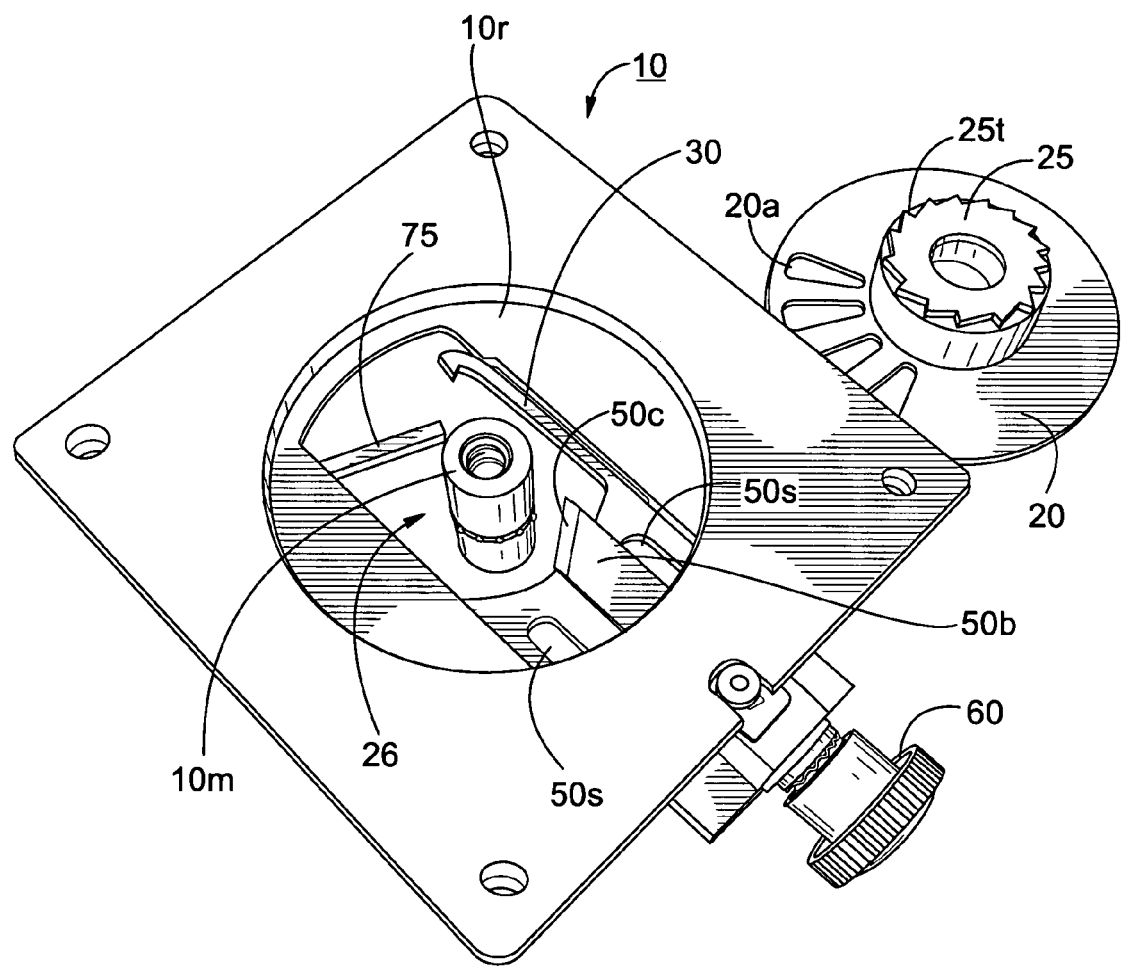
FIG. 10B is a bottom perspective view of the device shown in FIG. 10A according to embodiments of the present invention.
Figure 12:
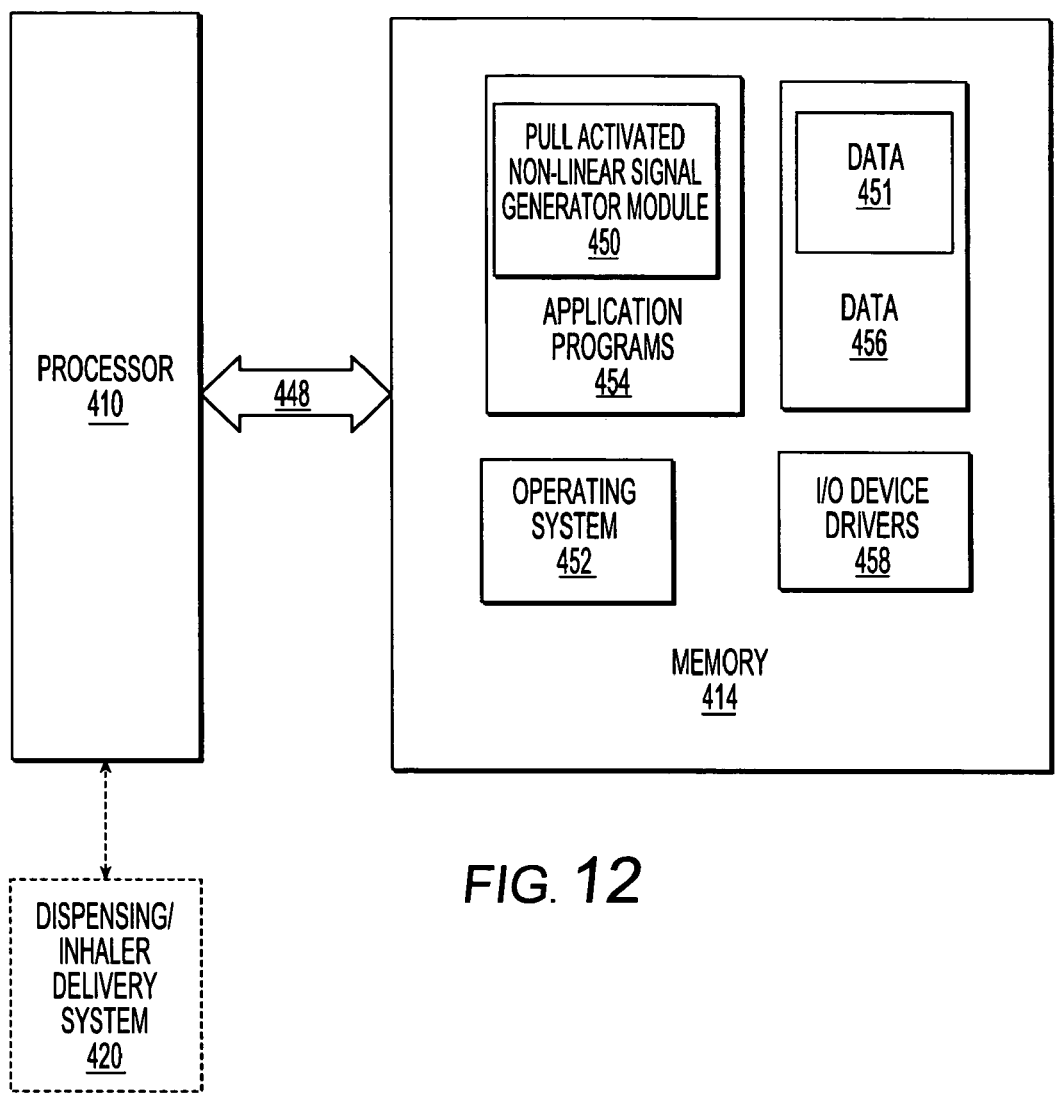
FIG. 12 is a block diagram of a data processing/control system with computer program code according to embodiments of the present invention.

As shown in FIGS. 10A and 10B, the blade 50b can have a substantially planar body while FIGS. 3A-3G illustrate that the cutting cartridge 50 can include a three-dimensional body with a forward portion 50f having a leading cutting edge 50c that transitions into a plow 51 and then a channel and/or chamber 52ch as will be discussed further below.

Figure 3G:
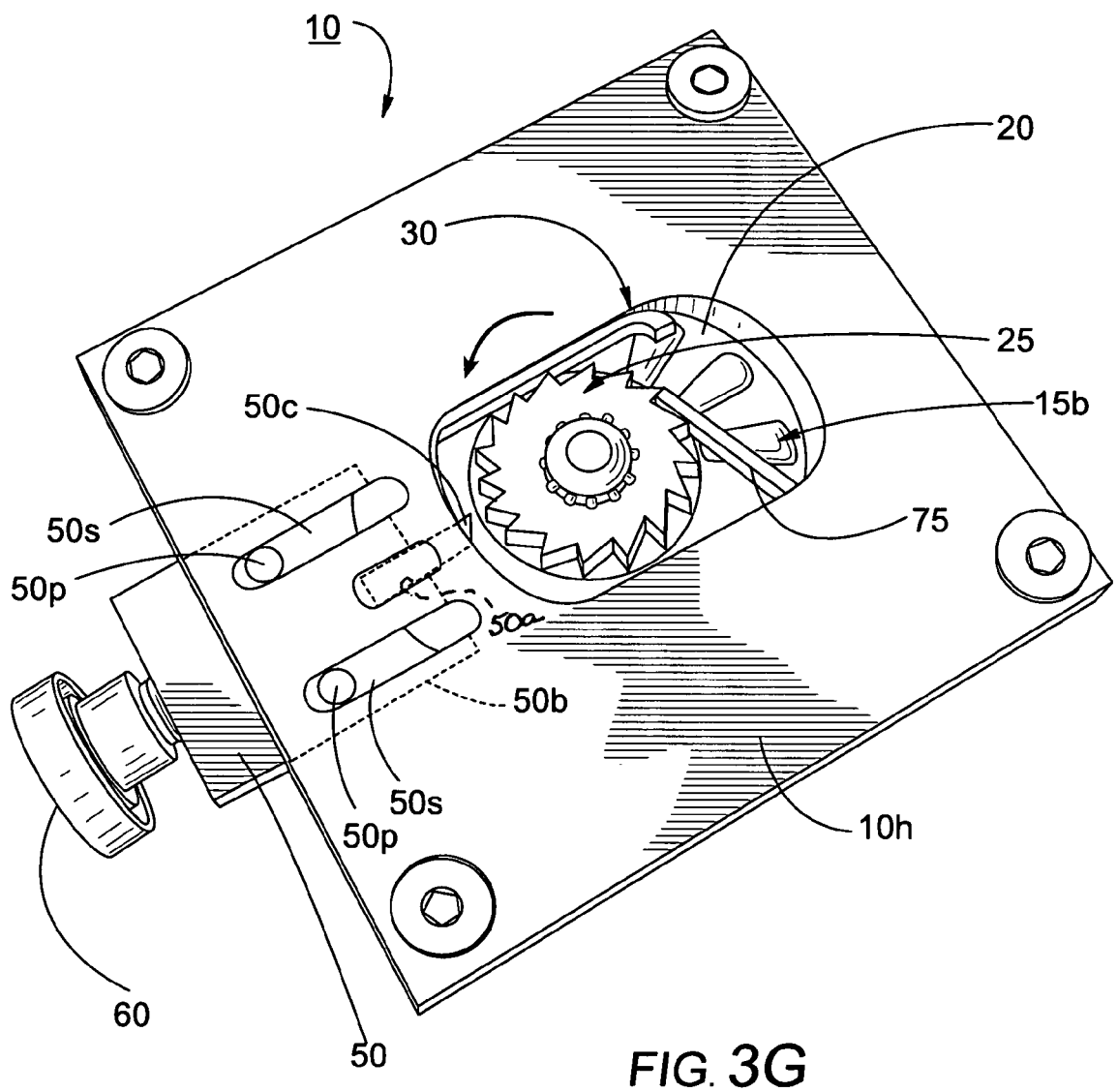
FIG. 3G is a top perspective view of a prototype of an inhaler with a cutting cartridge configured in an outward position according to embodiments of the present invention.
Figure 3H:
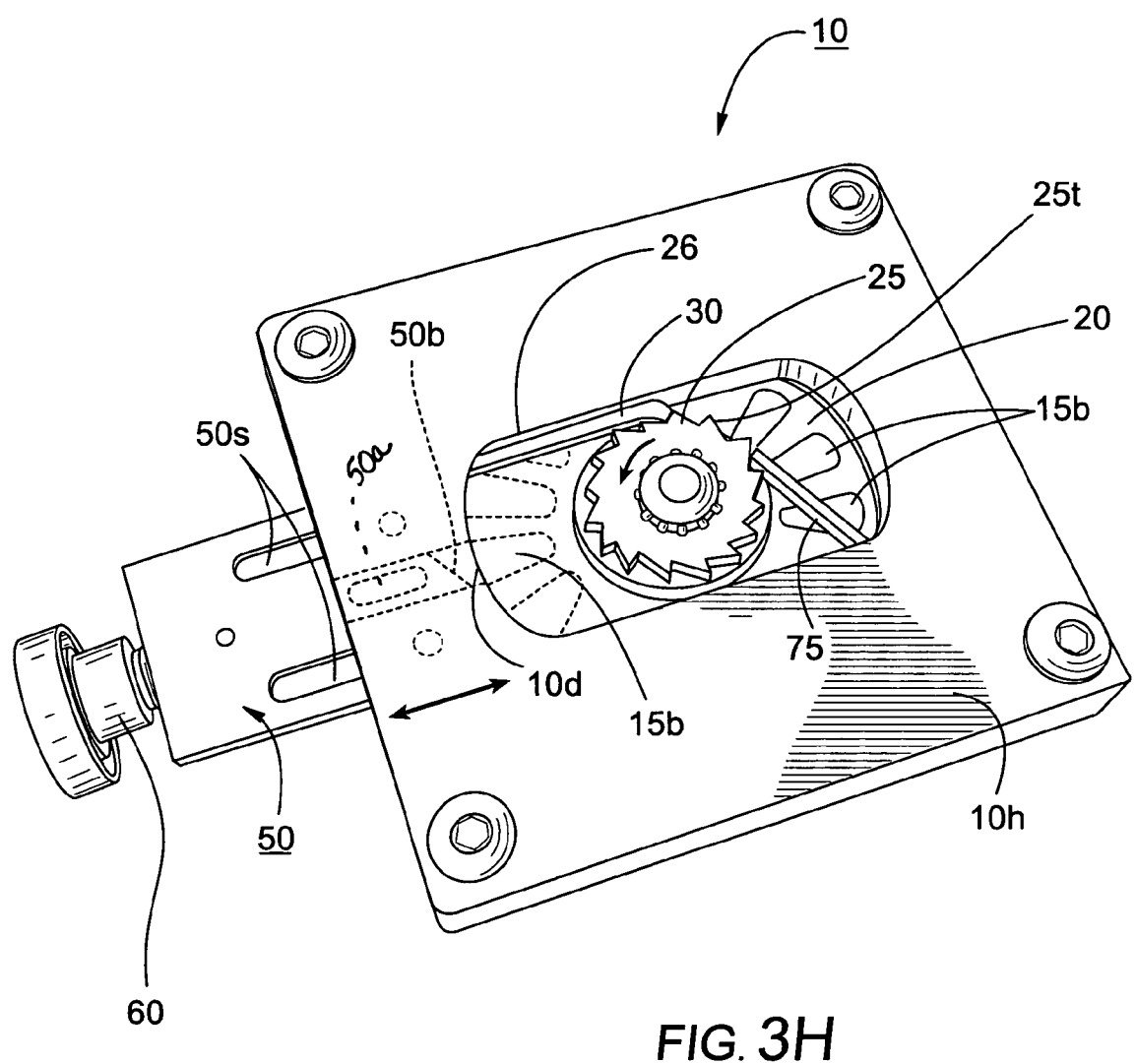
FIG. 3H is a top perspective view of the device shown in FIG. 3G with the cutting cartridge translated to an inward position according to embodiments of the present invention.

In certain embodiments, as shown in FIGS. 3G and 3H, the inhaler 10 can have a body with a gear window 26 formed to allow the gear to extend therein, above the upper primary surface of the frame 20 and blister package 15. In the embodiment shown in FIG. 3H, the blister dispensing position 10d is aligned with the blade 50b and the blister 15b located in this position is illustrated for clarity in cross-hatched lines. FIGS. 3G and 3H also illustrate that the cutting cartridge 50 may include slots 50s that engage with pins 50p mounted to that inhaler housing 10h to allow the cutting cartridge 50 to move back and forth in an aligned travel path. FIG. 3H illustrates that the cutting cartridge 50 may include the pins 50p and the inhaler housing 10h hold the slots 50s to allow the cutting cartridge 50 to move back and forth in the aligned travel path. Other translation configurations can also be used, such as, but not limited to, a channel formed in the inhaler housing 10h that is configured and sized to slidably receive the cutting cartridge 50 therein.

As shown in FIGS. 3A and 3C, the inhaler 10 can include a recessed shoulder 10s which is sized and configured to allow the mouthpiece 60 to securely slide back and forth thereoverwith a snug fit. Other translation configurations and mechanisms may also be used.

In certain embodiments, the inhaler 10 can be configured with an elongated body that can have a thin profile when viewed from the side with substantially planar top and bottom surfaces. See, e.g., FIG. 3F and co-pending and co-assigned U.S. patent application Ser. No. 10/434,009, the contents of which are hereby incorporated by reference as if recited in full herein. As used herein, the term "thin" means less than about 1.5 inches thick, and more preferably is about 1 inch or less in width (the width "W" being the distance between the top and bottom primary surfaces). The elongated body 10h can be configured to be pocket-sized (fitting into standard pockets on male and/or female clothing). By using substantially planar primary surfaces and/or a thin profile, the inhaler device 10 may be less obtrusively worn (less conspicuous) and/or more conformal to the body and less intrusive in clothing pockets. In certain embodiments, the length of the elongated body is between about 2-5 inches, typically under about 4.25 inches with the width being about 2-4 inches, typically about 2.5 inches.

In operation, as shown for example with reference to FIGS. 3E and 3F (which illustrates the inhaler 10 in a retracted or closed position), the inhaler 10 can be configured so that the mouthpiece 60 is in fluid communication with a substantially closed flow path 10f extending from the opened blister 15b underlying the cutting cartridge aperture 50a, through a cutting cartridge housing 52 (which can define at least a portion of the exit flow channel 52ch), to the mouthpiece orifice 60p and then to user as shown in FIG. 3G. The flow path 10f may include a positive air orifice or port 52p that can direct air to flow over and/or into the blister 15b to help excite the dry powder therein, prior to inspiration. The air orifice or port 52p may be configured on a forward edge portion of the body of the cutting cartridge 52 as shown. In particular embodiments, the air orifice 52p may be axially aligned with the exit flow channel upstream of the blister 15b.

Figure 4A:
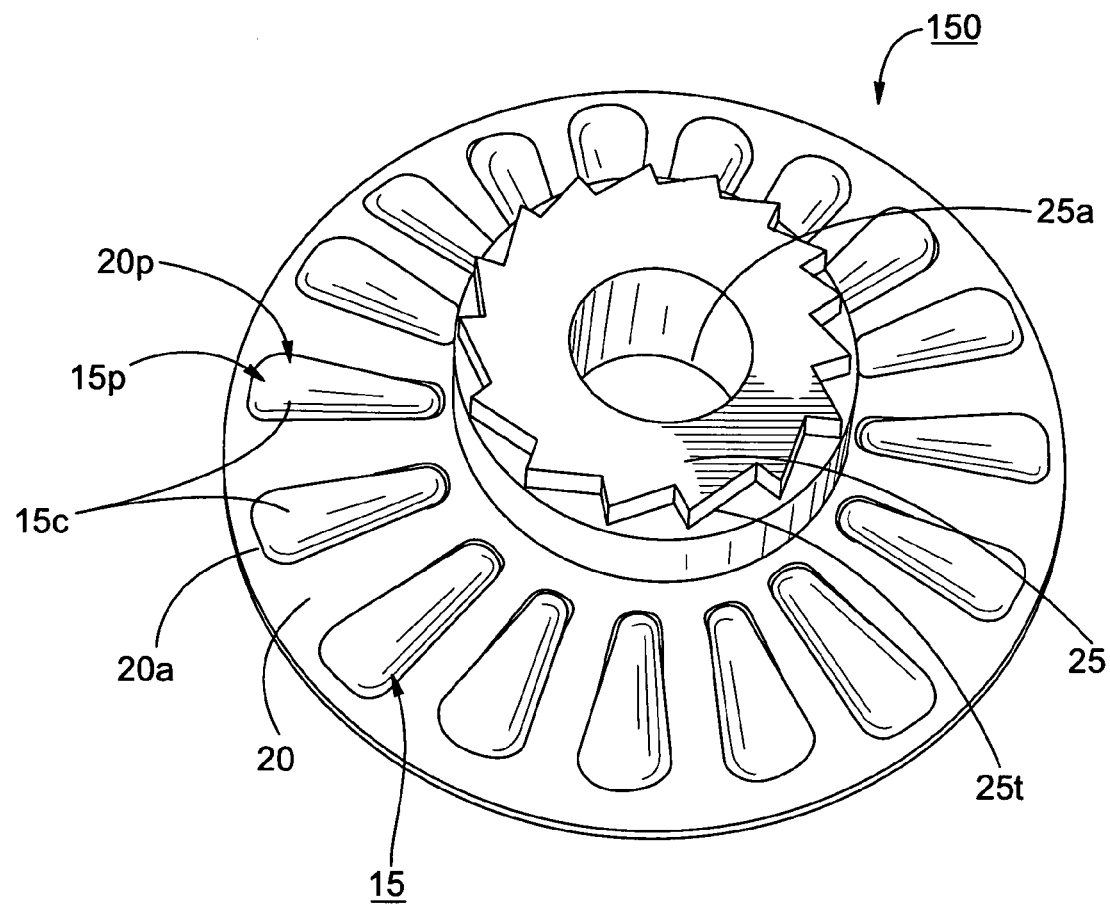
FIG. 4A is a top perspective view of a blister package with a frame according to embodiments of the present invention.
Figure 5B:
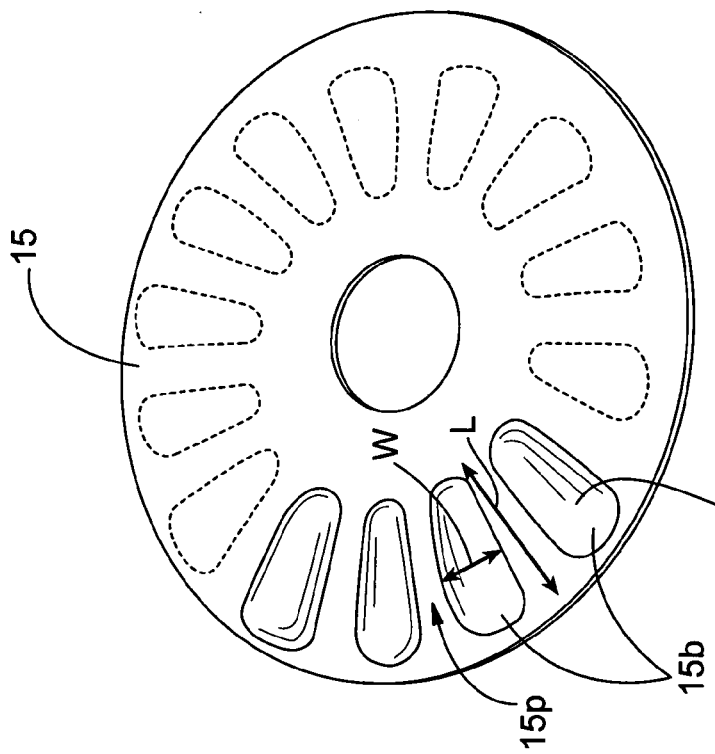
FIG. 5B is a top perspective view of the blister package shown in FIG. 4A according to embodiments of the present invention.
Figure 5C:
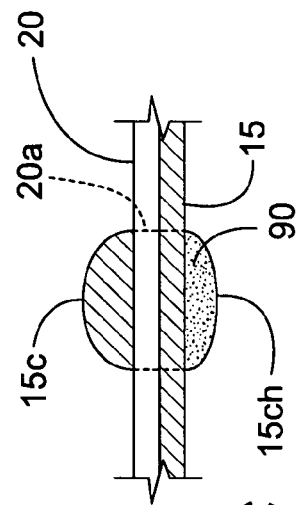
FIG. 5C is a front view of a partial blister package illustrating a respective blister with a projecting ceiling extending above a blister frame according to embodiments of the present invention.
Figure 5A:
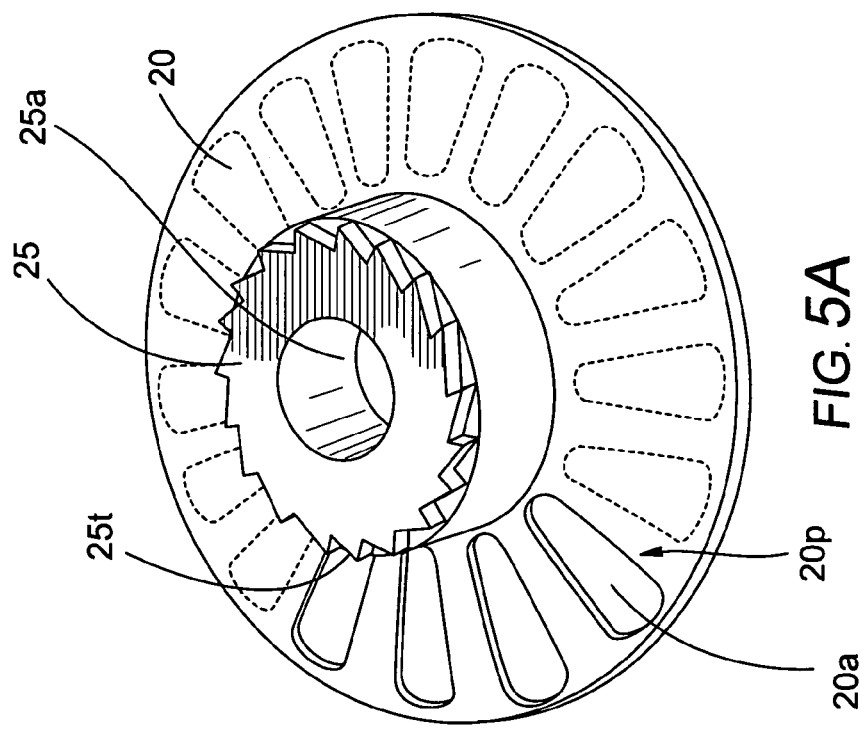
FIG. 5A is a top perspective view of the frame shown in FIG. 4A according to embodiments of the present invention.

FIG. 5B illustrates that the blister package 15 can be a multi-dose dry powder drug package with a plurality of circumferentially spaced-apart elongated blisters 15b, each sealed with a quantity of dry powder product disposed therein. FIG. 5A illustrates the blister frame 20 separate from the blister package 15. The blister frame 20 can have increased rigidity relative to the blister package, and in certain embodiments can be substantially rigid. The blister frame 20 can be configured to overlie the blister package 15, as shown. In other embodiments, the blister frame 20 may underlie the blister package 15 (not shown). In yet other embodiments, the frame 20 can be configured to sandwich the blister package 15 between upper and lower frame members (not shown) to hold the blister package 15 in the inhaler 10. FIG. 5C illustrates a sample blister configuration when viewed from the outside end of the blister package 15. The floor of the blister channel 15ch may be recessed (as shown) or substantially planar such as shown in FIG. 4C.

The blister frame 20 can, in particular embodiments, include the gear 25 thereon. The gear 25 may be integrally mounted to or formed on the blister frame 20 or may be releaseably mounted thereto. The gear 25 can include a bore 25a that can receive a pin or other mounting member to attach the gear 25 and frame 20 to the inhaler 10. As shown in FIG. 4A, the blister frame 20 and blister package 15 may be configured as a replaceable modular unit 150. In particular embodiments, the blister frame 20, the gear 25 and the blister package 15 are disposable after the blisters have been depleted and the inhaler is configured to allow replacement. In other embodiments, the entire inhaler 10 can be disposable after the blisters have been depleted (i.e., the dry powder and/or medicament dispensed).

In the embodiment shown in FIG. 4A and FIG. 5A, the frame 20 can include a plurality of frame apertures 20a, each with a perimeter shape 20p. The perimeter shape 20p is sized and configured to allow the projecting ceiling 15c of the blister 15b to extend therethrough. The frame aperture perimeter shape 20p may be configured to substantially correspond to the blister perimeter shape 15p when viewed from the top. Thus, the frame aperture 20a may have a shape and size that is substantially the same as the shape and size of a respective blister 15b. The blister 15b can have a width and length as shown in FIG. 5B and the aperture 20a can have substantially the same width and length (typically just a bit larger than the width/length of the blister).

As shown in FIG. 5C, the blister package 15 resides under the frame 20 with the projecting ceiling 15c of a respective blister 15b on the blister package 15 rising above the frame 20 through an aligned corresponding frame aperture 20a. As shown, the underside of the blister 15b may be configured with a recessed channel 15ch. It is noted that in certain of the figures (such as shown in FIGS. 3A, 4A, 5A and 5B), the blister package 15 and the frame 20 are illustrated without a complete set of blisters 15b and frame apertures 20a thereon. Typically, the blister package 15 will have a full set of blisters 15b substantially equally circumferentially spaced apart about a disk configuration and the frame 20 will have a corresponding number of apertures 20a, correspondingly spaced, also with a disk configuration.

FIGS. 4B and 4C illustrate an alternative blister package 15' configuration. As shown, the blister package 15' includes four layers, a ceiling 15c that includes the projections, a spacer layer 15sp that defines at least a portion of sidewalls of the blister channel, a floor 15fl and a piezoelectric polymer 15pz. The spacer 15sp includes apertures 15a that define the sidewalls of the channel 15ch. The apertures 15a can be formed so that the sidewalls angle out from the bottom to the top. For additional description of blister packages, see copending Provisional U.S. Patent Application Ser. Nos. 60/514,733 and 60/605,484, the contents of which are hereby incorporated by reference as if recited in full herein.

In certain embodiments, visible indicia and/or audible alerts can be used to warn a user that he/she is approaching the last of the filled blister inhalant doses on the blister package 15 and/or to indicate that the dose was properly (and/or improperly) inhaled or released from the inhaler device 10. For example, certain dry powder dose sizes are formulated so that it can be difficult for a user to know whether they have inhaled the medicament (typically the dose is aerosolized and enters the body with little or no taste and/or tactile feel for confirmation). Thus, a sensor can be positioned in the exit flow path and configured to be in communication with a digital signal processor or microcontroller, each held in or on the inhaler 10. In operation, the sensor is configured to detect a selected parameter, such as a difference in weight, a density in the exiting aerosol formulation, and the like, to confirm that the dose was released. The sensor (or another sensor) may also be configured to detect flow rate or inspiratory effort of the user to assess whether to acknowledge that the dose was properly released/inspired. For example, a "green" light can be activated notifying a user that the dose was properly released or an audio acknowledgement (such as by transmitting a prerecorded message or a predetermined tone) can notify the user that the dose was properly released. Similarly, an visual and/or audio warning or alert can be generated when a dose was not properly released so that a user can determined whether to re-inspire the dose or activate a different blister.

In addition, the blister package 15 can include color-enhanced markings for the last few (such as the last 5) doses. The color-enhanced markings may change from darker (orange to salmon or red) or to completely different colors as the last dose or last few doses approach. Alternatively (or additionally), the multi-dose disposable package 15 may be configured with audible alert features that activate a digital signal processor or micro-controller (not shown) housed in the elongated body 10 to generate a stored audible warning (such as "warning, refill needed, only five doses remain") when a desired number of doses have been administered.

In addition, in certain embodiments, the inhaler 10 can include a dose alert with a timer/clock which monitors the time of the last dose taken and/or provides an audible tactile and/or visual alert to remind a user when a next planned dose is approaching. For example, if a medicament is prescribed to be taken every 8 hours, the inhaler 10 can be pre-programmed with this dose plan or configured to accept a user's input to define same. Upon dispensing, the inhaler 10 can automatically store in memory the time of the dispensing. The timer can then track when the next dose is due. The inhaler 10 can be configured to store the time and date of each dose dispensed so that a clinician can review the therapeutic activity and/or response based on adherence to a treatment plan. The inhaler 10 can include a computer download port (such as an RS232) that can provide this data to a clinician at an office visit and/or remotely such as over a global computer network. The inhaler 10 may also include input regarding a patient's body condition with a time/date stamp (that may be automatically computer generated by the inhaler) that records other information of interest, including blood sugar/glucose measurements, a patient's notation of feeling low blood sugar, low energy, nausea, dizziness, wheezing, respiratory ability, or other reaction or condition. Thus dosing, a time in relation to a patient's feeling, condition, activity level and the like can be correlated with the time a medicament is delivered, for analysis. This information may allow a clinician to ascertain side effects, efficacy and/or a patient's adherence to a planned treatment, without requiring that a patient take notes or write in a diary. The inhaler 10 may also be configured to integrate certain testing devices to perform and then automatically record certain test results (i.e., analysis of a body analyte such as blood).

Figure 6A:
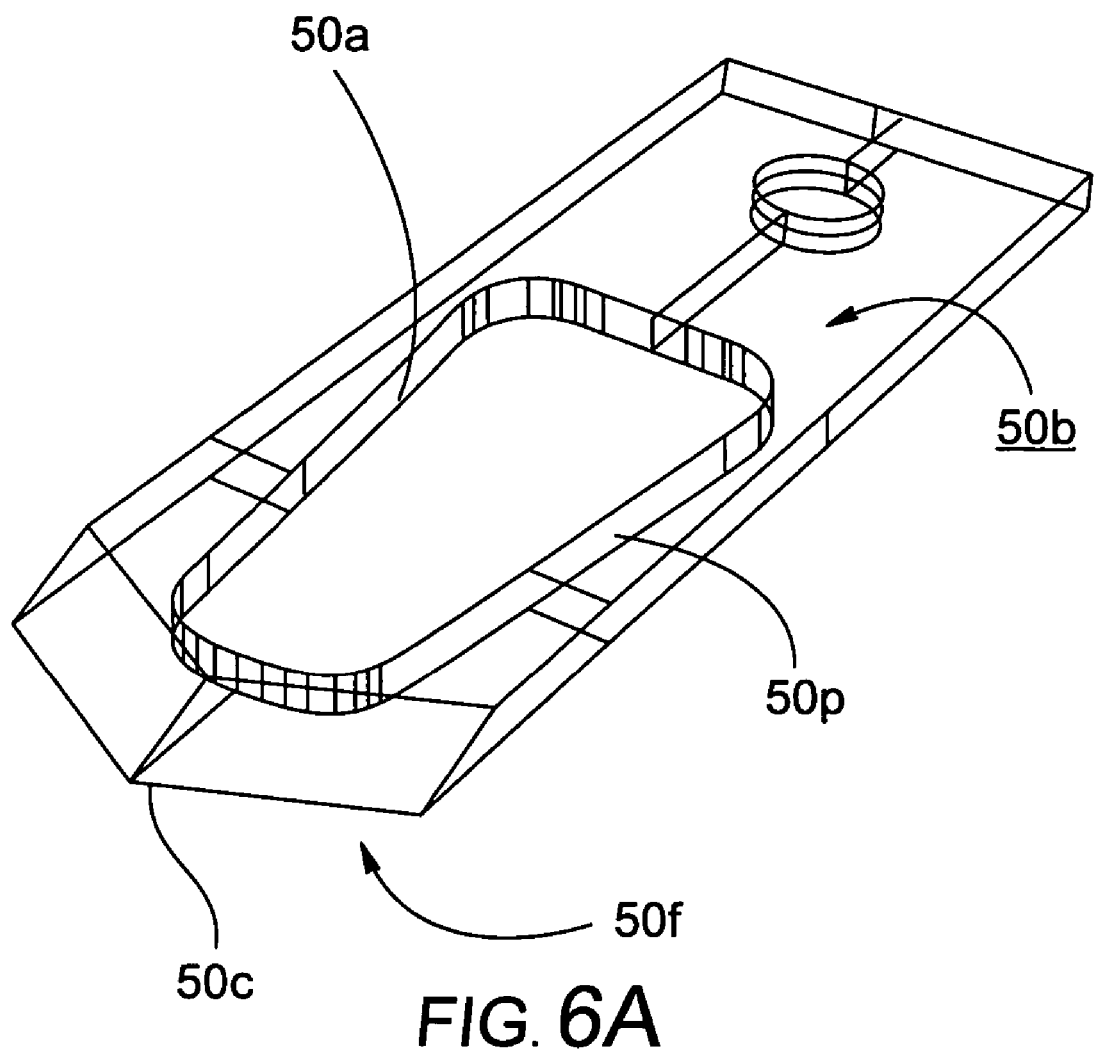
FIG. 6A is a side perspective view of a cutting member according to embodiments of the present invention.

Referring now to FIG. 6A, an embodiment of a blade 50b configured to mount to the cutting cartridge 50 illustrated in FIG. 3A is shown. The blade 50b includes a forward or leading (cutting 50c) edge portion 50f that is configured to open (typically cut or slice) at least a portion of the projecting ceiling 15c of a blister 15b. In operation, the blade 50b travels generally (typically substantially) parallel to a plane extending horizontally about an upper portion of the underlying blister channel 15ch along a length direction thereof at a position that is less than the height of the blister projection, to slice a major portion of the ceiling 15c in the length direction, forming a gap space 15o such as shown in FIG. 6C. As shown in FIG. 6C, once opened, the gap space 15o is sized to allow the dry powder 90 held in the blister 15b to be dispensed via the opening space 15o. FIG. 6D illustrates an alternate opened configuration of the blister 15o according to certain particular embodiments of the present invention. The blade 50b may be configured with a width that is less than the width of the ceiling 15c and/or frame aperture 20a and, in operation, move above the frame 20 and below and across the uppermost portion of the ceiling 15c to open the blister 15.

Referring again to FIGS. 6A and 6B, in certain embodiments, the forward portion 50f of the blade 50b can be configured with a beveled cutting edge 50c having a substantially center forwardmost point that angles outward when viewed from the top, as shown in FIG. 6B. In other embodiments, the forward portion of the blade 50f may be configured with a point located on an edge and which angles outwardly therefrom when viewed from the top (FIG. 10A). The forward or leading edge portion of the blade 50f may also rise vertically at a minor angle (typically less than about 30, and more typically less than about 15 degrees from the forward edge) to the upper surface thereof. Other blade configurations may also be used. In particular embodiments, the blade 50b may rest or slide on the upper primary surface of the frame 20 as it cuts and opens the blister 15b.

In certain embodiments, the blade 50b may be configured with a limited stroke so that the forwardmost portion 50f of the blade 50b stops (in the inward position), before it reaches the innermost portion of the blister 15i (the portion facing the gear). In other embodiments, the blade 50b is configured so that the forward edge portion 50f travels beyond the innermost portion of the blister 15i, typically so that the innermost portion of the blade aperture 50a aligns with the underlying innermost portion of the frame aperture 20a.

Figure 7A:
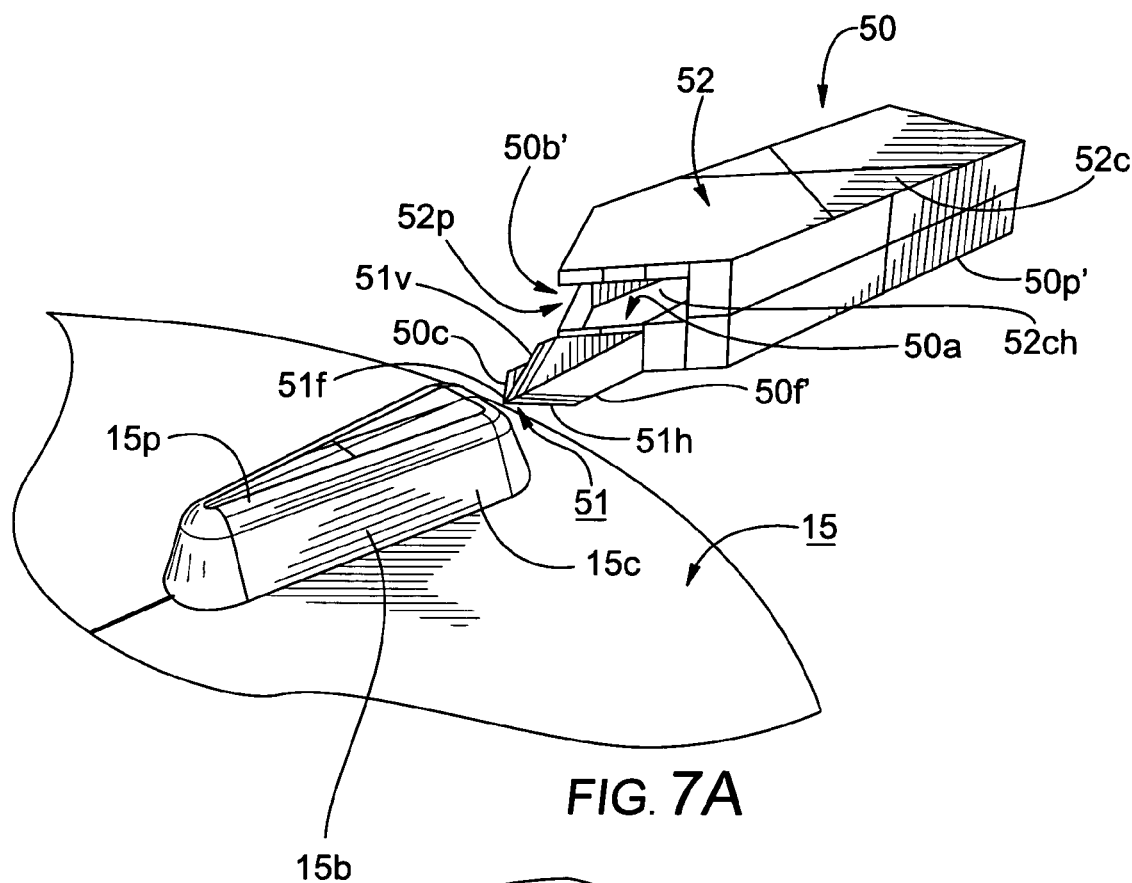
FIG. 7A is a side perspective view of a cutting cartridge aligned with a blister on a blister package according to embodiments of the present invention.
Figure 7B:
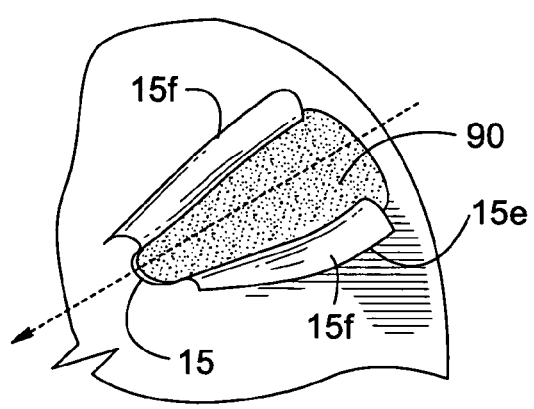
FIG. 7B is a side perspective view of a blister with an opened ceiling formed by the device shown in FIG. 7A according to some embodiments of the present invention.
Figure 7C:
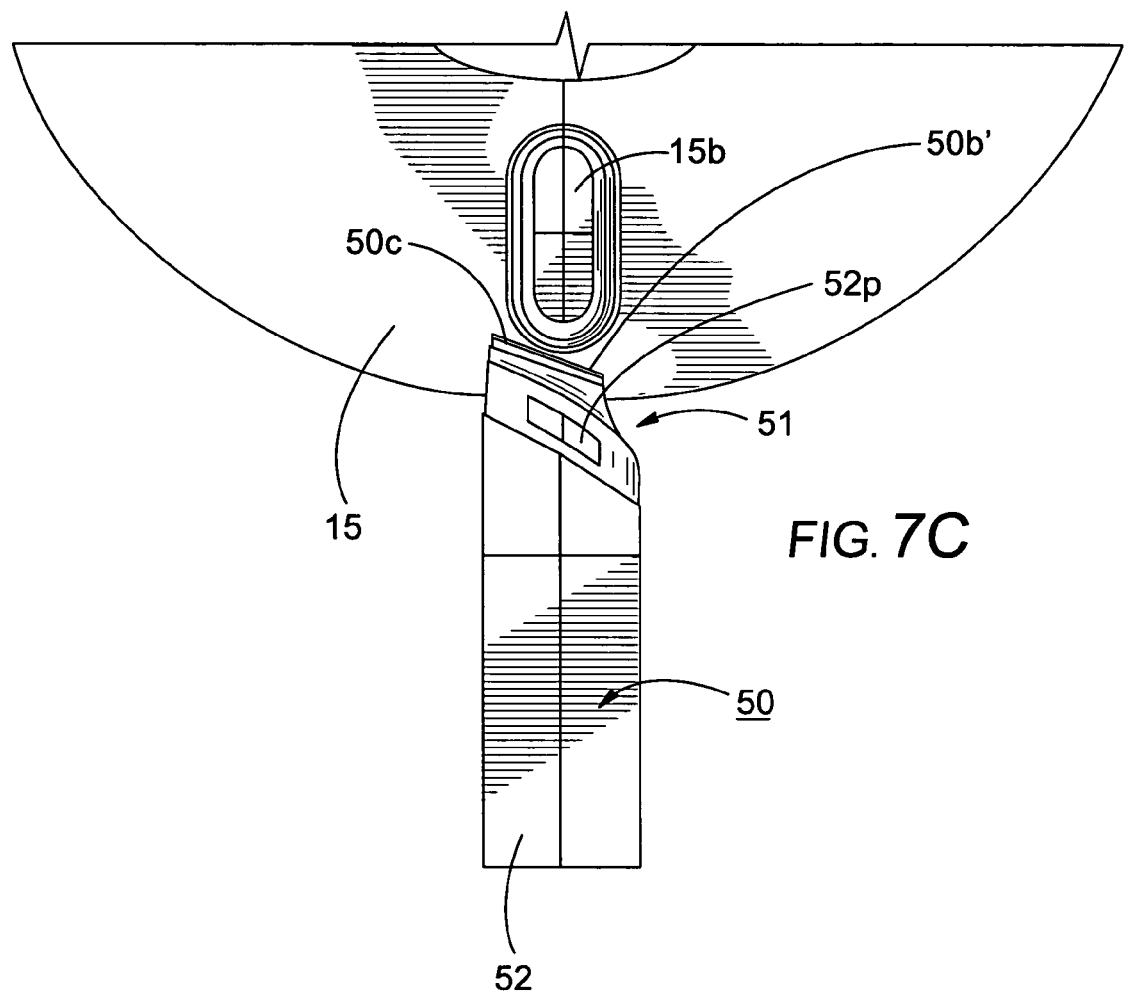
FIG. 7C is a top view of the cutting cartridge shown approaching an aligned/indexed blister according to embodiments of the present invention.
Figure 7D:
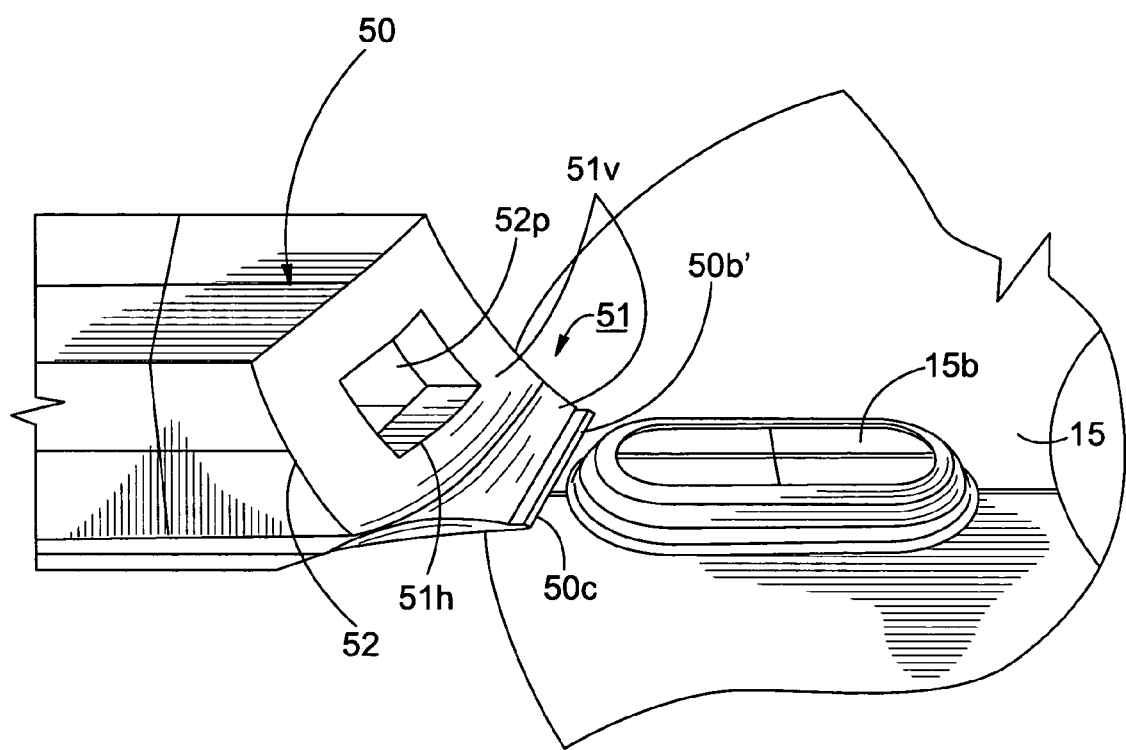
FIG. 7D is a side view of the cutting cartridge shown in FIG. 7C according to embodiments of the present invention.

FIG. 7A illustrates an alternate embodiment of a cutting cartridge 50 having a forward portion 50f' with a plow (also described as a plow mechanism) 51 with a leading cutting edge 50c. The plow 51 is configured to lift, push, form and/or force at least one loose edge portion 15e to fold over into a folded edge configuration, such as the two-fold configuration shown in FIG. 7B, as the cutting edge 50c of the blade 50b' advances across the blister 15b at a height that is below the uppermost height of the projecting blister 15p. That is, the plow 51 can lift the loose blister ceiling material and fold the lifted ceiling material back (typically flat onto underlying blister material, similar to an open page in a book) as the cutting cartridge 50 advances (retracts into the inhaler 10). In some embodiments, the plow 51 can have a leading cutting edge 50c that may be configured and aligned to be offset from the lengthwise centerline of the target indexed blister 15b and, in operation, fold a single separated loose blister edge over to form a single folded flap to thereby open the blister (not shown).

In certain embodiments, the cutting edge 50c of the blade 50b' can be configured to travel across the blister 15b at a height that is proximate the base of the projecting blister ceiling 15p above the frame 20. In particular embodiments, the lower primary surface of the cutting edge 50c may rest or slide on the upper primary surface of the frame 20 as the cutting cartridge 50 advances and slices or cuts and parts the blister 15b.

As shown in FIG. 7A, the plow 51 can include a forwardmost portion 51f that includes a vertical angularly rising edge portion 51v that may rise relatively quickly from the cutting edge 50c at the forwardmost portion of the blade 50b' at an angle of greater at than about 30 degrees (when viewed from the side). The forwardmost portion 50f of the cutting edge is shown as a centrally located point in FIG. 7A, but can be configured otherwise. The forwardmost vertical portion 51v of the plow 51 can be configured with a pointed (sharp) edge, a blunt edge or rounded edge. The plow or plow mechanism 51 can also include a planar (typically horizontal) portion 51h that increases in width relative to the forwardmost point 51 (i.e, that fans outwardly when viewed from the top as shown in FIGS. 9A and 9B).

Figure 8A:
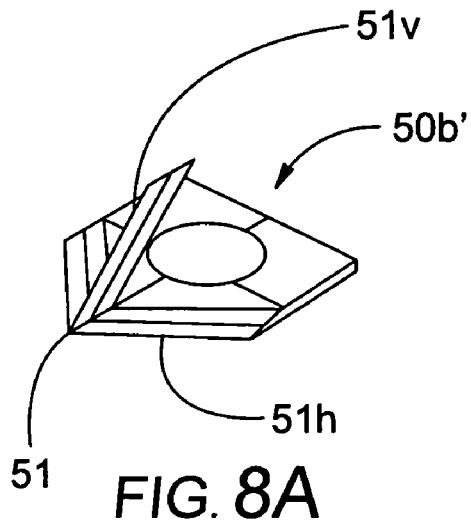
FIG. 8A is a side perspective view of a forward cutting edge portion of the device shown in FIG. 7A.
Figure 8B:
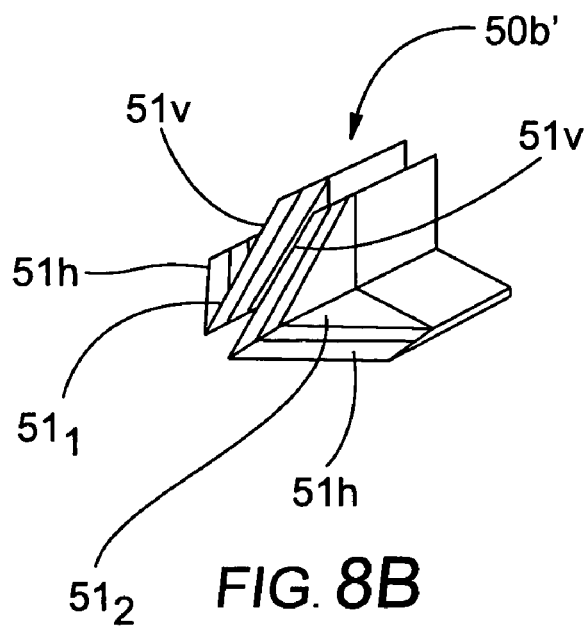
FIG. 8B is a side perspective view of an alternative cutting edge portion for a device such as shown in FIG. 7A.
Figure 9A:
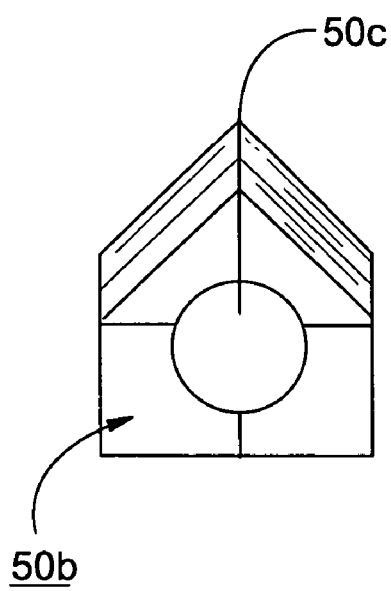
FIG. 9A is a top view of the device shown in FIG. 8A.
Figure 9B:
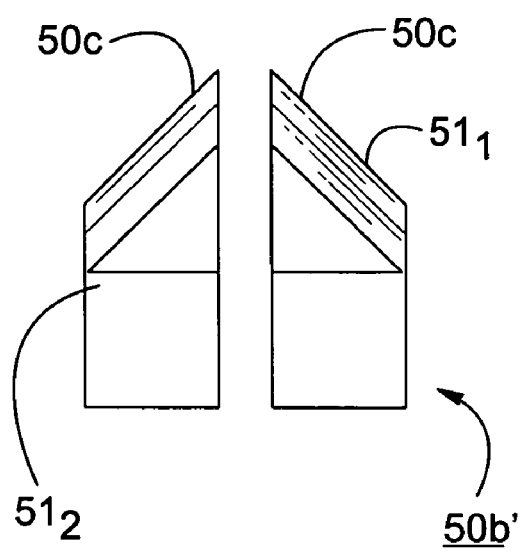
FIG. 9B is a top view of the device shown in FIG. 8B.

FIGS. 8A and 9A illustrate the blade 50b' shown in FIG. 7A. FIGS. 8B and 9B illustrate an alternate embodiment. In this embodiment, the plow 51 can include two forward spaced apart blade portions $51_1$, $51_2$, each with a respective vertical edge portion 51v and horizontal edge portion 51h. In other embodiments, the plow 51 can be configured with one of the two blade portions shown in FIGS. 8B and 9B. Other suitable plow configurations can also be used.

Referring again to FIG. 7A, the plow 51 is shown attached to a cartridge body 52. The cartridge body 52 is sized and configured to reside over the opened blister as when the forward blade portion has traveled across the aligned blister 15b to its resting location. The bottom portion of the cartridge body 52 includes an aperture 50a with a perimeter 50p'. The perimeter 50p' is sized and configured with a shape that is sufficient to enclose the underlying blister perimeter (15p, FIG. 5B). The aperture 50a can be configured with a perimeter shape that substantially corresponds to that of the blister 15p (FIG. 5B). The body of the cartridge 52 has a ceiling 52c that encloses (typically seals) the underlying opened blister and forms a chamber 52ch with a port 52p that is in fluid communication with the mouthpiece 60. Although the port 52p is shown as being at an inward portion of the cartridge body 52, it may also be positioned at other locations in the inhaler to be in communication with the open blister but not impede proper inspiratory flow of the dry powder to the user during inhalation. For example, the port 52p may be positioned on the cutting cartridge body 52 proximate a ceiling or floor portion thereof but configured so that the port 52p is beyond the underlying blister boundary or perimeter 15p during dispensing.

FIGS. 7C-7G illustrate another example of a cutting cartridge 50 with a plow 51 configuration according to embodiments of the present invention. As shown, the blade 50b' can include a substantially planar cutting member that defines the cutting edge 50c (FIG. 7E) that extends beneath and a relatively short beyond the plow 51. Typically the cutting edge 50c extends beyond the forward portion of the cutting cartridge body 52 less than about 3 mm, and more typically, less than about 1 mm.

Figure 7E:
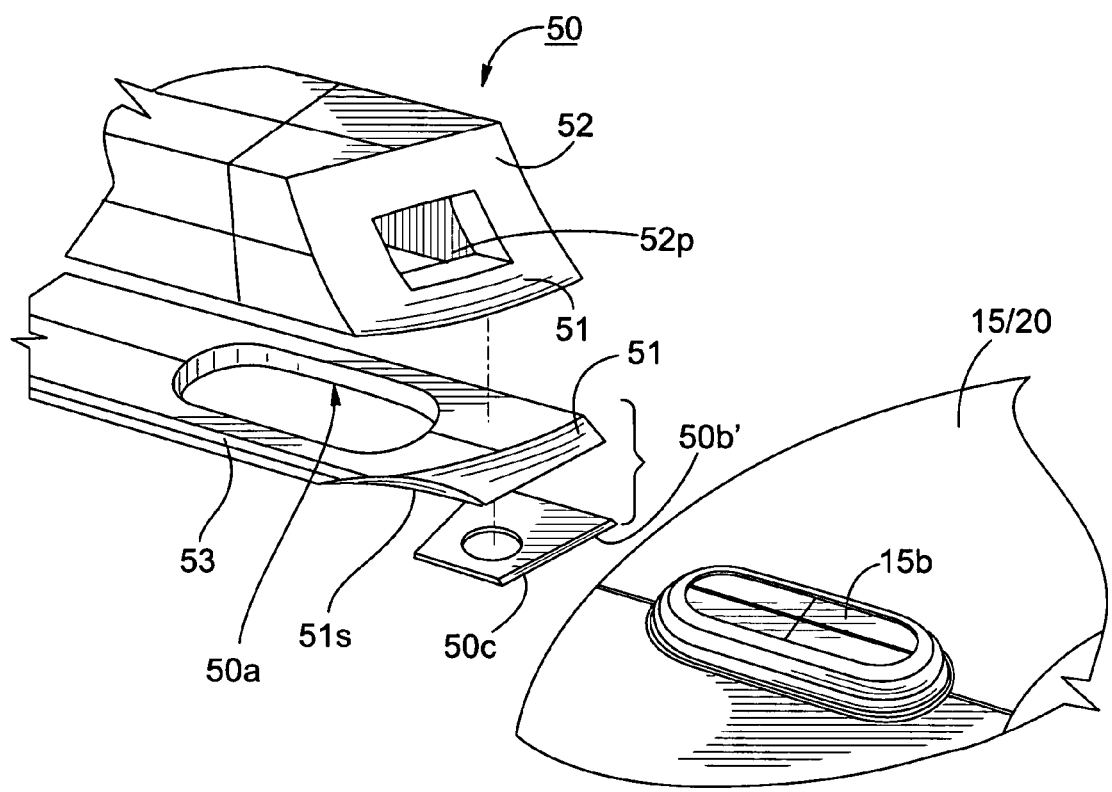
FIG. 7E is an exploded view of the cutting cartridge shown in FIG. 7C according to embodiments of the present invention.
Figure 7F:
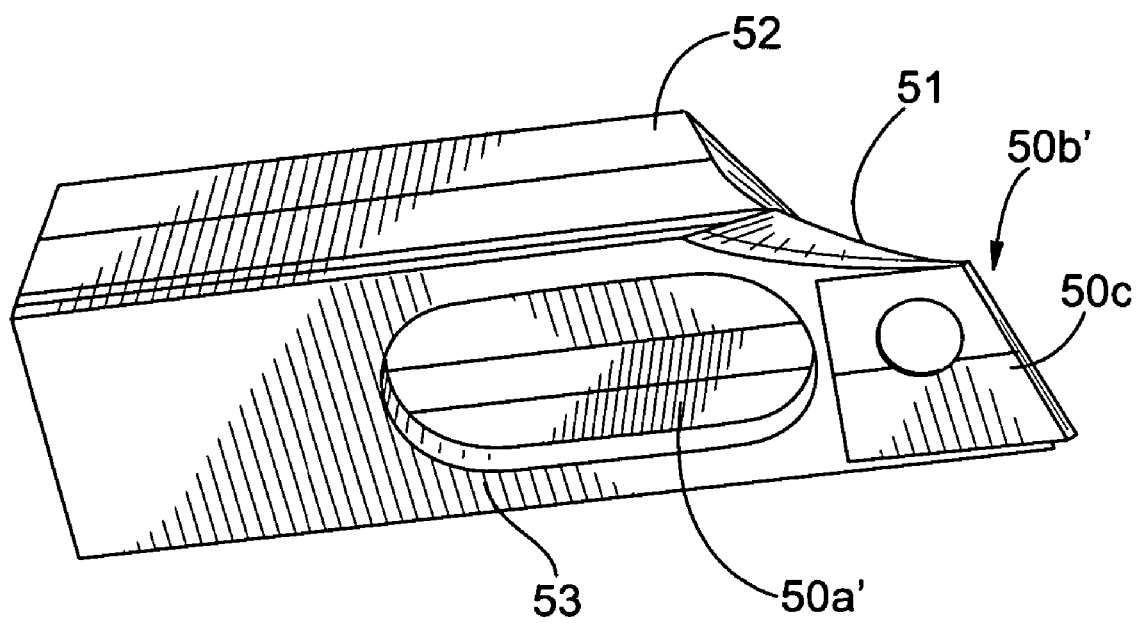
FIG. 7F is a bottom view of the cutting cartridge shown in FIG. 7C according to embodiments of the present invention.

As described above, in operation, the cutting cartridge 50 advances in a generally lengthwise direction across the indexed blister 15 to slice and/or separate the ceiling material 15c thereon, then lifts the loose edge of the separated ceiling material and folds it over. FIG. 7E illustrates that the cutting cartridge 50 may include three attached components, a leading cutting blade 50c configured to define the leading cutting edge, an intermediate body 53 that defines the bottom of the cutting cartridge 50, and the top body 52. The intermediate body 53 and the upper cartridge body 52 can have a greater length than that of the cutting blade 50c. The intermediate body has a lowermost portion that has the aperture 50a' formed therein. The cartridge body 52 overlies and seals the intermediate body 53 to form the substantially enclosed channel 52ch.

As shown by the inner channel represented in broken line in FIG. 3E, the channel 52ch may extend to the mouthpiece orifice 60p to define the flow exit inspiratory channel 10f. The cutting cartridge body 52 may also include forward port 52p. That is, the channel 52ch can be configured to form at least a portion of the exit flow path to capture and direct the bolus of dry powder from the open blister to the user, without releasing dry powder into non-target regions of the inhaler (via the port 52p).

Figure 7G:
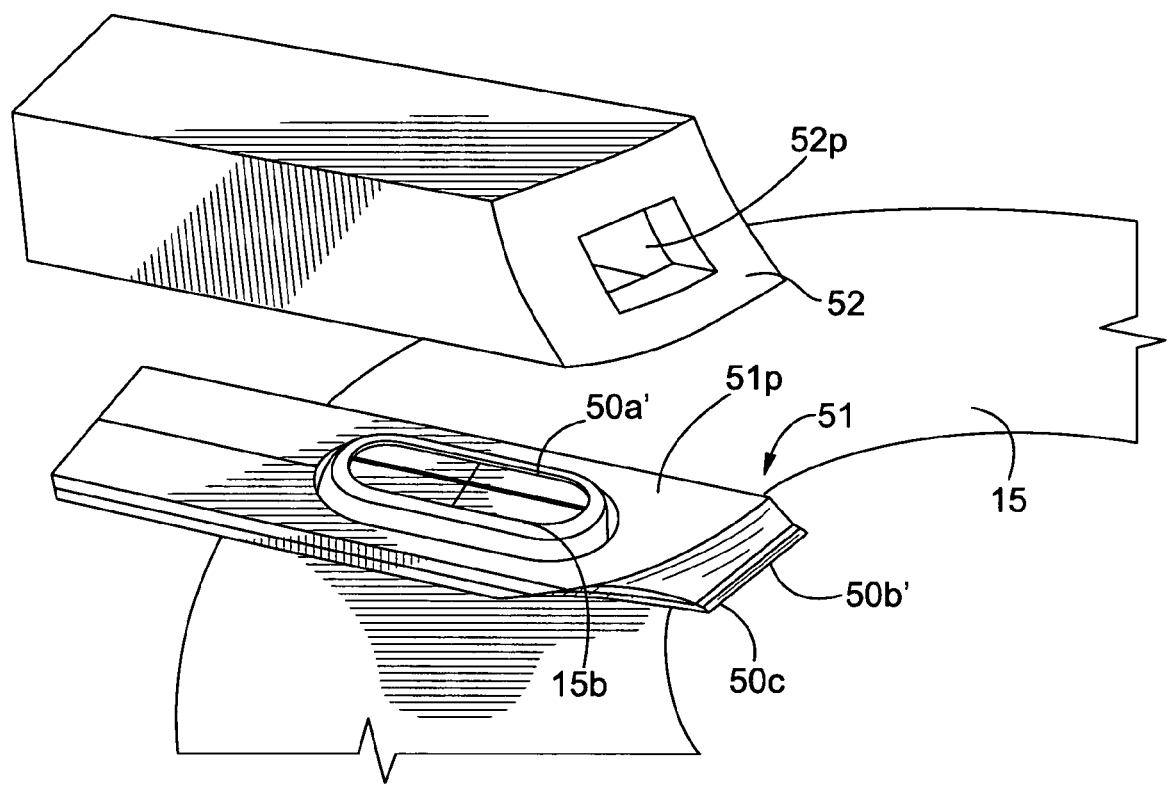
FIG. 7G is a partially exploded view of the cutting cartridge shown in FIG. 7C as the cartridge surrounds an underlying blister according to embodiments of the present invention.

The plow 51 can be formed by the joined forward portions of the cutting edge 50c and the two upper components 52, 53 of the blade 50b'. However, in other embodiments, the plow 51 may be otherwise formed, such as formed integrally with the body of the cartridge 50. As shown in FIG. 7E, one lateral edge portion 51s of the plow 51 may have a scooped out portion that, in operation, can fold, form and/or push the lifted ceiling material out and down. FIG. 7G illustrates an exploded view of the cutting cartridge 50 aligned with the indexed blister 15b (shown without the blister ceiling open) with the cutting cartridge aperture 50a' positioned over and surrounding the perimeter of the underlying indexed blister 15b for dispensing.

FIGS. 10A and 10B illustrate an exemplary bottom configuration of the inhaler 10 shown in FIGS. 3A and 3B. FIG. 10A illustrates the frame 20 attached to the inhaler 10 without the blister package 15 for clarity. In this embodiment, the cutting cartridge 50 is shown with the blade 50b configured to stop at a stop location 10st that is prior to the innermost edge portion of the aligned blister 15b so that the sliced blister material remains securely attached at the inward edge 15i as shown, for example, in FIG. 6D.

FIG. 10B illustrates the inhaler 10 with the frame 20 (and blister package 15) removed showing the gear window 26, a mounting member 10m, a recess 10r and the cutting blade 50b in the inward position.

As discussed above, the blister package 15 can be configured so that the floor comprises a piezoelectric material, which can be electrically activated to vibrate the blister channel 15ch to facilitate aerosolization upon inspiration. The vibration can be initiated prior, during and/or after the blister 15b is opened. In certain embodiments, the vibration can occur before (for priming), during and after the blister 15b is opened. Air can be introduced into the open blister via port 52p to help excite the dry powder in the blister 15b as discussed above. In particular embodiments, the floor of the blister 15 can include a piezoelectric polymer material configured with a downwardly projecting channel (i.e., projecting in the opposite direction as the ceiling 15c). As will be described further below, the piezoelectric polymer material can be deposited, coated, sprayed, inked, foiled, or otherwise layered with a metallic conductive material at selected regions of the package 15 and along at least a portion of each of the elongated channels 15ch to define a vibrating or flexing active region when activated by an excitation voltage. The ceiling 15c may comprise a material that has sufficient rigidity to retain the projecting shape as discussed above. The ceiling 15c may comprise foil material, polymer material, or combinations of same.

FIG. 11A illustrates an example of an amplitude-modified vibratory signal suitable for vibrating the blister channel 15b holding the dry powder 90. The vibratory signal can include a kHz carrier frequency (such as about 5 kHz-50 kHz) modified by low modulating frequency (typically about 10-200 Hz). The frequency of the vibration can be modified to match or correspond to the flow characteristics of the dry powder substance held in the package to attempt to reach a resonant frequency(s) to promote uniform drug dispersion into the body. In certain embodiments, the vibration of the active piezoelectric surfaces in the channel 15ch may be on the order of about 10-200 Hz. In certain embodiments, the frequency may be between at about 10-60 Hz. The vibration can be influenced by the amount of active surface and the excitation voltage pulses applied thereto as well as the channel geometry. During dispensing, a channel 15ch can be activated by providing a voltage across the piezoelectric layer. In certain embodiments, the voltage provided may be at about 100-400 volts peak-to-peak, typically between about 200-400 volts peak-to-peak. In other embodiments, the voltage can be applied at a different level and at other various frequencies, such as at higher frequencies of between about 25 kHz to about 2 MHz. Additional suitable excitation signals will be discussed further below. In certain embodiments, the signal and/or the vibration of the energy provided to the channel 15ch may be configured to concurrently or successively rapidly vibrate the dry powder at a plurality of different frequencies (at similar or different amplitudes) in the range of between about 10 Hz-1000 kHz. In certain particular embodiments, the frequencies are between about 10-200 Hz, such as 10-60 Hz. In other embodiments, they may be in the range of between about 7 kHz-100 kHz, such as 7.5 kHz or more such as frequencies between about 15 kHz to 50 kHz.

In some embodiments, as schematically shown in FIGS. 11B-11D, a non-linear powder-specific dry powder vibratory energy signal (shown as a different powder specific signal for each of the simulated illustrated formulations shown as "A", "B" and "C") comprising a plurality of selected frequencies can be generated (corresponding to the particular dry powder being currently dispensed) to output the particular signal corresponding to the dry powder then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

FIGS. 11B-11D illustrate three different dry powders $215_1$, $215_2$, $215_3$, each of which can be analyzed and/or characterized ($20ch_1$, $20ch_2$, $20ch_3$, respectively). Customized or corresponding individual (non-linear) input signals $20s_1$-$20s_3$ with frequencies selected from the corresponding characterization that are specifically targeted to that dry powder to facilitate fluidic flow during dispensing can be determined for each dry powder $215_1$, $215_2$, $215_3$. The drug-specific signals are shown by the signals $20s_1$-$20s_3$.

The inhalers 10 include signal-generating circuitry therein in communication with the channels 15ch. The signal generating circuitry may be programmed with a plurality of predetermined different input signals, or if the inhaler dispenses only a single dry powder, the signal generator may be programmed with a single signal. Appropriate powder-specific signals can be determined experimentally and/or computationally at an OEM or evaluation site and input into the inhalers (via hardware and/or software components including programmable processors). For additional description of signals and operations to determine same, see co-pending and co-assigned U.S. patent application Ser. Nos. 10/434,009, 10/606,678, 10/607,389, and 10/606,676: the contents of these applications are hereby incorporated by reference in their entireties as if recited in full herein.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may be include a plurality (typically at least three) superpositioned modulating frequencies and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

In certain embodiments, the piezoelectric polymer material, which is included in the blister packages 15 of embodiments of the invention, is formed from a piezoelectrically active material such as PVDF (known as KYNAR piezo film or polyvinylidene fluoride) and its copolymers or polyvinylidene difluoride and its copolymers (such as PVDF with its copolymer trifluoroethylene (PVDF-TrFe)).

In particular embodiments, the piezoelectric polymer material comprises a layer of a thin PVDF film. As used herein, the term "thin film" means that the piezoelectric polymer layer is configured as a structurally flexible or pliable layer that can be sized to be about 10-200 μm thick. In certain embodiments, the piezoelectric polymer layer can be sized to be less than about 100 μm thick, and more typically, about 20-60 μm thick.

As noted above, selected regions of the piezoelectric polymer material can be coated or layered with a conductive material to form a desired conductive pattern. The conductive regions (at least portions of the blister regions) of the package 15 define the active regions and can be individually or selectively activated during operation. Laminates of PVDF and another material capable of being formed into and holding a desired blister shape and/or powder channel may be particularly suitable for forming the active blister configurations. Suitable laminates include thin film layers of PVDF united to thin layers of one or more of aluminum, PVC and nylon films. The PVDF may form the bottom, top, or an intermediate layer of the laminated material structure. For intermediate layer configurations, vias and/or edge connections can be used to apply the electric signal to the blister piezoelectric material.

The metal trace patterns can be provided by applying a conductive pattern onto one or more of the outer faces of the piezoelectric substrate layer. For depositing or forming the metal, any metal depositing or layering technique can be employed such as electron beam evaporation, thermal evaporation, painting, spraying, dipping, or sputtering a conductive material or metallic paint and the like or material over the selected surfaces of the piezoelectric substrate (preferably a PVDF layer as noted above). Of course, alternative metallic circuits, foils, surfaces, or techniques can also be employed, such as attaching a conductive mylar layer or flex circuit over the desired portion of the outer surface of the piezoelectric substrate layer. If flex circuits are used, they may be configured or attached to the piezoelectric substrate layer so as to be substantially transparent to the structure of the sensor array to reduce any potential dampening interference with the substrate layer.

Typically, upper and lower surface metal trace patterns are formed on opposing sides of a piezoelectric polymer material layer but do not connect or contact each other. For example, conductive paint or ink (such as silver or gold) can be applied onto the major surfaces of the package about the elongated channels and associated metal traces such that it does not extend over the perimeter edge portions of the piezoelectric substrate layer, thereby keeping the metal trace patterns on the top and bottom surfaces separated with the piezoelectric substrate layer therebetween. This configuration forms the electrical excitation path when connected to a control system to provide the input/excitation signal for creating the electrical field that activates the deformation of the piezoelectric substrate layer during operation.

As such, the electrical path for each elongated channel 15*ch* extends via the respective upper and lower transmission lines to the electrical terminations operably connected to the controller. The excitation circuit (signal generating circuitry) configuration can be such that the upper trace operates with a positive polarity while the lower trace has a negative polarity or ground, or vice versa (thereby providing the electric field/voltage differential to excite the piezoelectric substrate in the region of the selected channel 15). Of course, the polarities can also be rapidly reversed during application of the excitation signal (such as + to −, or + to −) depending on the type of excitation signal used, thereby flexing the piezoelectric material in the region of the receptacle portion. For a more complete discussion of the active excitation path or configuration, see U.S. application Ser. No. 10/204,609 (incorporated by reference hereinabove).

Generally describing some embodiments, in operation, the dry powder inhalers of the present invention have integrated, active energy piezoelectric polymer substrate multi-dose drug packages that generate patient-assisted dispersal systems. The inhalers can be used for nasal and/or oral (mouth) respiratory delivery. The inhalable dry powder doses can be packaged in a multi-dose dry powder drug package that includes a piezoelectric polymer substrate (such as PVDF) that flexes to deform rapidly and provide mechanical oscillation in an individually selectable signal path on the package. The signal path directs the signal to the region of the drug receptacle or well to cause the well to oscillate in cooperation with a user's inspiratory effort, and, thus, actively direct the dry powder out of the well and up into the exit flow path. The airflow rate and/or volume of a patient may be measured in situ dynamically during administration and the DPI can include a control system that provides adjustable energy output to the active piezoelectric polymer substrate dispersal element responsive to a user's inspiratory capabilities. In addition, the DPI control system may be a multi-purpose system that can administer a plurality of different types of dry powder substances, or formulations, such as different drugs. As such, the control system may be configured to adjust the energy delivered to the piezoelectric polymer substrate based on the type of substance and/or the flowability of the dry powder substance or drug being administered. The energy may be adjusted in situ based on considering both the user's inspiratory effort and the type of substance being administered. As a result, the powder can be actively dispersed into the exit flow path using a suitable DCS (drug containment system) of the inhaler during the user's inspiratory activity without using pressurized propellants such as CFC's.

In addition, the piezoelectric polymer material may be configured as two piezoelectric polymer film layers separated by an intermediately positioned pliable core, all of which are concurrently deformable to flex by the application of voltage thereacross.

FIG. 12 is a block diagram of exemplary embodiments of data processing systems that illustrates systems, methods, and/or computer program products in accordance with embodiments of the present invention. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 12, the memory 414 may include several categories of software and data used in the data processing system 405: the operating system 452; the application programs 454; the input/output (I/O) device drivers 458; a pull-activated powder (specific) signal generator (vibratory) module 450; and the data 456. The data 456 may include: (a) a look-up chart/table data for dry powder signal formulations for plurality of different dry powders 451; (b) in situ acquired measurement data whether to confirm that the dry powder dose was properly (or improperly) dispensed and/or patient inspiratory data, which may be obtained from an operator or stored by the inhaler; (c) and/or timing data that automatically activates the signal and inputs to the blister for dispensing the dry powder based upon a pull operation (pulling the cutting cartridge and/or mouthpiece outward). As will be appreciated by those of skill in the art, the operating system 452 of the inhaler and/or programmable inputs thereto may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/0 device drivers 458, and other software programs that may reside in the memory 414.

While the present invention is illustrated, for example, with reference to the powder signal generator module 450 being an application program in FIG. 12, as will be appreciated by those of skill in the art, other configurations may also be utilized while still benefiting from the teachings of the present invention. For example, the module 450 may also be incorporated into the operating system 452, the I/O device drivers 458 or other such logical division of the data processing system 405. Thus, the present invention should not be construed as limited to the configuration of FIG. 12, which is intended to encompass any configuration capable of carrying out the operations described herein.

The I/O data port can be used to transfer information between the data processing system 405 and the inhaler dispensing system 420 or another computer system or a network (e.g., the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 12 but is intended to encompass any configuration capable of carrying out the operations described herein.

The flowcharts and block diagrams of certain of the figures herein illustrate the architecture, functionality, and operation of possible implementations of dry powder-specific dispensing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the powder specific vibration energy signals are non-linear and the inhaler can include computer program code that automatically selectively adjusts the output of the vibration energy signal based on the identified dry powder being dispensed. The vibration energy output signals for the dry powders being dispensed can be based on data obtained from a fractal mass flow analysis or other suitable analysis of the dry powder being administered to the user. The inhaler may be particularly suited to dispense low-density dry powder.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dry powder inhaler with a multi-dose dry powder package for dispensing pharmaceutical grade formulations of inhalable dry powder, comprising:
    an inhaler housing;
    a blister package held in the housing, the blister package comprising a plurality of spaced apart sealed blisters thereon, each blister having a projecting ceiling and a floor defining a blister channel therebetween, the blister channel comprising a dry powder therein;
    a blister indexing mechanism in communication with the blister package to position a blister in a dispensing position;
    a movable blade cartridge mounted in the housing configured to hold a blade at a forward portion thereof; and
    an extendable mouthpiece attached to the movable blade cartridge, wherein, in operation, a user extends the mouthpiece outward and then retracts the mouthpiece inward to cause the blister package to advance thereby positioning a blister in the dispensing position in the inhaler, the retraction causing the blade cartridge to move the blade lengthwise across a blister ceiling held in the dispensing position in the inhaler to open the blister held in the dispensing position.

2. A dry powder inhaler according to claim 1, wherein the blister channels have a width, depth, and length, and wherein the blade is configured to travel in the inhaler above and across at least a major portion of the length of a respective channel, substantially horizontally.

3. A dry powder inhaler according to claim 1, wherein, in operation, a forwardmost portion of the blade stops traveling inward into the inhaler before the blade reaches an innermost edge portion of blister.

4. A dry powder inhaler according to claim 1, wherein, in operation, a forwardmost portion of the blade travels beyond the innermost edge portion of the blister.

5. A dry powder inhaler according to claim 1, wherein the indexing mechanism comprises a rotatable gear that cooperates with the mouthpiece and the blister package to advance the blister package a desired distance to position a blister in the dispensing position in the inhaler.

6. A dry powder inhaler according to claim 5, wherein the indexing mechanism further comprises a pawl that is attached to the mouthpiece and positioned in the inhaler so as to engage the gear and rotate the blister package a predetermined distance to serially advance blisters toward the dispensing position when the mouthpiece is extended outward.

7. A dry powder inhaler according to claim 5, wherein the indexing mechanism includes a gear window sized and configured to hold the gear therein, wherein the pawl is located about an outer perimeter of one side of the gear window and configured and sized so as to contact and advance at least one gear tooth forward when the mouthpiece is extended outward.

8. A dry powder inhaler according to claim 7, further comprising a locking arm extending into the gear window and configured to abut a portion of a gear tooth of the gear at a position that is spaced apart from the pawl to inhibit the gear from rotating backward when the mouthpiece is retracted inward.

9. A dry powder inhaler according to claim 8, wherein the pawl is configured to engage the gear in one rotating direction only when the mouthpiece is extended and to disengage the gear when the mouthpiece is retracted.

10. A dry powder inhaler according to claim 5, wherein the blister package is circular, wherein the gear is a rotatable gear substantially centrally mounted on a substantially rigid blister frame, the gear and frame being attached to the blister package to form a disposable blister and gear package assembly that is replaceable in the inhaler when the dry powder in the blisters on the package has been dispensed.

11. A dry powder inhaler according to claim 10, wherein the substantially rigid blister frame comprises apertures sized and configured to allow the projected ceilings of the blister package to extend therethrough.

12. A dry powder inhaler according to claim 1, wherein the blade cartridge has a plow-shaped forward edge portion.

13. A dry powder inhaler according to claim 12, wherein the plow-shaped forward edge portion has a leading cutting edge portion with a lateral portion that spans out horizontally and a vertical portion that rises at an angle of greater than about 30 degrees.

14. A dry powder inhaler according to claim 12, wherein the blade cartridge has a body with a flow channel formed therein, and wherein, in operation, dry powder flows through from the opened blister through the blade cartridge flow channel to the user.

15. A dry powder inhaler according to claim 1, wherein the blister package comprises a foil-containing ceiling having sufficient rigidity to be formed into and retain the ceiling projection shapes.

16. A dry powder inhaler according to claim 1, wherein the inhaler has an elongate body with a thin profile defining a pocket-sized inhaler that fits into the pocket of a garment worn by a user, wherein the floor of each blister comprises at least one thin piezoelectric polymer material layer with conductive selected portions in electrical communication therewith to define active energy releasing vibratory blister channels, and wherein, in operation, the blisters are adapted to be selectively activated to vibrate upon receipt of an electrical input.

17. A dry powder inhaler according to claim 1, wherein the blister package further comprises a substantially rigid spacer member disposed intermediate the projecting ceiling and the floor, the spacer having a plurality of spaced apart apertures, a respective aperture sized and configured to define sidewalls of a respective blister channel.

18. A dry powder inhaler according to claim 1, wherein the dry powder is a low-density dry powder.

19. A dry powder inhaler with a multi-dose dry powder package for dispensing pharmaceutical grade formulations of inhalable dry powder, comprising:

an inhaler housing;

a blister package held in the housing, the blister package comprising a plurality of spaced apart sealed blisters thereon, each blister having a projecting ceiling and a floor defining a blister channel therebetween, the blister channel comprising a dry powder therein;

a blister indexing mechanism in communication with the blister package to position a blister in a dispensing position;

a movable blade cartridge mounted in the housing configured to hold a blade at a forward portion thereof; and an extendable mouthpiece attached to the movable blade cartridge, wherein, in operation, a user extends the mouthpiece outward and then retracts the mouthpiece inward to cause the blister package to advance thereby positioning a blister in the dispensing position in the inhaler, the retraction causing the blade cartridge to move the blade lengthwise across a blister ceiling held in the dispensing position in the inhaler to open the blister held in the dispensing position, wherein the blisters have a perimeter shape, and wherein the blade is configured with a center aperture with a perimeter shape and size that substantially corresponds to that of a respective blister so that, when the blade and the blister are in a dispensing position, the blade defines a portion of an inspiratory exit flow path for the dry powder in the opened blister.

20. A dry powder inhaler according to claim 19, wherein, during active dispensing, the blade overlies an opened blister with the blade center aperture substantially aligned with the perimeter of the target blister.

21. A dry powder inhaler according to claim 20, wherein the ceiling has a first width, and wherein the blade has a second width that is less than the width of the ceiling.

22. A dry powder inhaler according to claim 21, wherein the blade has a substantially planar body with a beveled forward edge that travels substantially horizontally to open a respective blister.

23. A dry powder inhaler according to claim 22, wherein the beveled edge has a minor angle such that the blade forward edge rises less than about 30 degrees.

24. A dry powder inhaler with a multi-dose dry powder package for dispensing pharmaceutical grade formulations of inhalable dry powder, comprising:

an inhaler housing;

a blister package held in the housing, the blister package comprising a plurality of spaced apart sealed blisters thereon, each blister having a projecting ceiling and a floor defining a blister channel therebetween, the blister channel comprising a dry powder therein;

a blister indexing mechanism in communication with the blister package to position a blister in a dispensing position;

a movable blade cartridge mounted in the housing configured to hold a blade at a forward portion thereof;

an extendable mouthpiece attached to the movable blade cartridge, wherein, in operation, a user extends the mouthpiece outward and then retracts the mouthpiece inward to cause the blister package to advance thereby positioning a blister in the dispensing position in the inhaler, the retraction causing the blade cartridge to move the blade lengthwise across a blister ceiling held in the dispensing position in the inhaler to open the blister held in the dispensing position; and an input signal generating circuit that is adapted to operatively serially engage each of the blisters, the input signal generating circuit configured to provide the electrical input to selectively flex a portion of a blister held in the dispensing location in the inhaler, responsive to the electrical input, wherein the inhaler has an elongate body with a thin profile defining a pocket-sized inhaler that fits into the pocket of a garment worn by a user, wherein the floor of each blister comprises at least one thin piezoelectric polymer material layer with conductive selected portions in electrical communication therewith to define active energy releasing vibratory blister channels, and wherein, in operation, the blisters are adapted to be selectively activated to vibrate upon receipt of an electrical input.

25. A dry powder inhaler according to claim 24, wherein, in operation, the electrical input is configured to flex a blister in the dispensing position by applying a non-linear vibration input signal thereto, and wherein the non-linear input signal is selected to represent a priori flow characteristic frequencies of the dry powder formulation held in the blister channel.

26. A dry powder inhaler according to claim 25, wherein the non-linear vibration input signal comprises a plurality of different selected frequencies that correspond to the flow characteristic frequencies of the dry powder formulation held in the package.

27. A dry powder inhaler according to claim 25, wherein the non-linear vibration input signal is formed by the superposition of the plurality of different selected frequencies.

28. A dry powder inhaler according to claim 27, wherein the input generating circuit is configured to flex the channels by applying an amplitude modulated frequency selected to represent a priori flow characteristic frequencies of the dry powder formulation held in the package.

29. A dry powder inhaler according to claim 25, wherein the non-linear input signal is a low energy input signal having a plurality of superpositioned modulating frequencies, and wherein the non-linear input signal comprises frequencies in the range of between about 10 Hz to 1000 kHz.

30. A dry powder inhaler according to claim 29, wherein the non-linear input signal comprises carrier frequencies in the range of between about 15 kHz to 50 kHz.

31. A method of dispensing dry powder from an inhaler, comprising:

extending a mouthpiece of an inhaler outward to automatically index a blister on a blister package into a dispensing position;

vibrating the indexed blister; and retracting the mouthpiece inward to open the indexed blister, wherein the retracting step comprises automatically advancing a cutting blade across a portion of a projecting ceiling of the indexed blister in the inhaler responsive to the retraction.

32. A method according to claim 31, further comprising moving the cutting blade in concert with the mouthpiece to open the projecting ceiling of the indexed blister responsive to the retracting step, wherein the blister package is circular.

33. A method according to claim 31, wherein the opening step comprises plowing across the ceiling with a member having a three-dimensional forward edge portion to substantially concurrently open and fold ceiling material as the blade travels across the blister.

34. A method according to claim 31, wherein the opening step comprises slicing a top horizontal portion of the blister ceiling as the blade moves across the ceiling in a direction that is generally aligned with a center axis extending in a length direction of an underlying blister channel.

35. A method according to claim 31, further comprising ceasing a forward movement of the cutting blade as the blade travels across a length of the ceiling before a forwardmost portion of the cutting blade reaches an innermost portion of the blister ceiling.

36. A method according to claim 35, wherein the cutting blade is configured to cut an opening in the blister ceiling that is less than the width of the ceiling.

37. A method according to claim 31, wherein the opening step comprises advancing a forwardmost portion of the cutting blade over an entire length of the ceiling so that a leading edge of the cutting blade resides outside a boundary of the opened blister.

38. A method according to claim 31, the method further comprising releasing dry powder in the opened blister to a user upon inspiration, wherein the inhaler blisters comprise a piezoelectric polymer, wherein the vibrating step comprises concurrently oscillating the piezoelectric polymer material, opening the blister; and wherein the inspiratory step comprises releasing inhalable dry powder aerosol to the user while the piezoelectric polymer is vibrating upon inspiration.

39. A method according to claim 38, wherein the vibrating step comprises oscillating the indexed blister to impart energy to dry powder held in a respective indexed blister cavity to cause the dry powder to vibrate at a desired amplitude modified frequency to facilitate delivery of an inhalable dry powder aerosol.

40. A method according to claim 39, wherein the oscillating step causes the dry powder to vibrate with a non-linear motion to facilitate delivery of an inhalable dry powder aerosol.

41. A method according to claim 40, wherein the oscillating step comprises a frequency that is between about 10-200 Hz.

42. A method according to claim 40, wherein the non-linear motion comprises a non-linear input signal at a low energy having a plurality of superpositioned modulating frequencies.

43. A method of dispensing dry powder from an inhaler, comprising:
    extending a mouthpiece of an inhaler outward to automatically index a blister on a blister package into a dispensing position;
    vibrating the indexed blister;
    retracting the mouthpiece inward to open the indexed blister; and
    moving a cutting blade in concert with the mouthpiece to open a projecting ceiling of the indexed blister responsive to the retracting step;
    wherein the extending step comprises rotating a gear attached to the blister package to index the blister in a dispensing position.

44. A method according to claim 43, further comprising:
    contacting the gear with a pawl to urge the gear in a first rotative direction toward the dispensing position during the extending step; and then
    automatically locking the gear to inhibit the gear from rotating in the reverse rotative direction during the retracting step.

45. A method of dispensing dry powder from an inhaler, comprising:
    extending a mouthpiece of an inhaler outward to automatically index a blister on a blister package into a dispensing position;
    vibrating the indexed blister; and
    retracting the mouthpiece inward to open the indexed blister,
    wherein the retracting step comprises automatically advancing a cutting blade across a portion of a projecting ceiling of the indexed blister in the inhaler responsive to the retraction,
    wherein the cutting blade comprises an aperture, and wherein the inhaler comprises a frame member with a gear and the blister package mounted to the frame member, the frame member having apertures that overlie and generally follow the perimeter shape of the blisters so that the blister projecting ceilings rise through respective frame apertures, the method further comprising aligning the cutting blade aperture to a respective one of the frame apertures over the indexed blister.

46. A method according to claim 45, further comprising forming a portion of an inspiratory exit flow path for the dry powder held in the opened blister using the aligned blade aperture over a respective frame aperture and the opened blister.

47. A method according to claim 45, wherein the the blister package is circular.

48. A blister packaging opening mechanism adapted for use in an inhaler, comprising:
    a translatable cutting cartridge having a body with an enclosed airflow channel therein and an airflow entry port defining an inspiratory exit flowpath, the cutting cartridge further comprising a cutting blade residing on a lower portion of the cutting cartridge with an aperture sized and configured to reside about a perimeter of an opened blister, the cutting blade aperture is configured to allow powder to flow up therethrough and into the cutting cartridge channel and wherein, the cutting cartridge is configured to mount to an inhaler and move forward in the inhaler to cause the cutting blade to slice lengthwise across a projecting ceiling portion of an aligned blister sealing a blister channel, traveling generally parallel to a plane drawn over an upper portion of the underlying blister channel, to open the blister for dispensing a dry powder medicament held therein.

49. A blister packaging opening mechanism for use in an inhaler, comprising:
    a translatable cutting cartridge having a forward plow portion with a cutting blade having an aperture that resides attached to a bottom portion of the forward plow portion, wherein the forward plow portion has an outer wall with an enclosed airflow channel therein and an airflow entry port defining an inspiratory exit flowpath, wherein, the cutting cartridge is configured to mount to an inhaler and move forward in the inhaler along a length direction of the blister to open and then fold at least one loose edge portion of a projecting ceiling of an aligned blister as the cutting cartridge advances to thereby open the blister for dispensing a dry powder medicament held therein, and wherein the cutting blade aperture resides over an opened blister and the powder from the opened blister flows therethrough and into the forward plow portion to then flowably exit the inhaler using the inspiratory exit flow path.

50. A blister packaging opening mechanism according to claim 49, the cutting blade has an elongate aperture, and wherein the airflow entry port resides above and upstream of the cutting blade.

51. A blister packaging opening mechanism according to claim 50, wherein the cutting blade aperture is sized and configured to snugly abut a perimeter of a respective blister.

52. A method for opening a sealed blister on a blister package, comprising:

advancing a plow mechanism across a sealed blister to open a projecting ceiling layer thereof to automatically lift and fold a loose edge portion of the opened ceiling layer, wherein the plow mechanism comprises a slicing blade with an aperture therein positioned at a bottom forwardmost portion thereof, and wherein the slicing step is carried out automatically in response to the advancing step;

slicing the sealed blister open and then using the plow mechanism to lift and fold the loose edge portion; and maintaining the plow mechanism in an advanced position so that the slicing blade aperture resides over a perimeter of the opened blister and a portion of the plow resides thereabove to define an enclosed portion of an exit airflow path for powder in the opened blister.

* * * * *